(12) United States Patent
Biggadike et al.

(10) Patent No.: US 7,947,727 B2
(45) Date of Patent: May 24, 2011

(54) COMPOUNDS

(75) Inventors: Keith Biggadike, Stevenage (GB); Anthony William James Cooper, Stevenage (GB); David House, Stevenage (GB); Simon John Fawcett MacDonald, Stevenage (GB); Philip Alan Skone, Stevenage (GB); Gordon Gad Weingarten, Stevenage (GB)

(73) Assignee: GlaxoGroupLimited, Greenford, Middlesex (GB)

( * ) Notice: Subject to any disclaimer, the term of this patent is extended or adjusted under 35 U.S.C. 154(b) by 0 days.

(21) Appl. No.: 12/444,713

(22) PCT Filed: Oct. 10, 2007

(86) PCT No.: PCT/EP2007/060777
§ 371 (c)(1),
(2), (4) Date: Apr. 8, 2009

(87) PCT Pub. No.: WO2008/043789
PCT Pub. Date: Apr. 17, 2008

(65) Prior Publication Data
US 2010/0120883 A1    May 13, 2010

(30) Foreign Application Priority Data
Oct. 13, 2006  (GB) .................. 0620385.5

(51) Int. Cl.
*A01N 43/56*   (2006.01)
*A61K 31/415*  (2006.01)
*C07D 231/56*  (2006.01)
(52) U.S. Cl. .............. 514/406; 514/885; 548/361.1
(58) Field of Classification Search ............ 514/406, 514/885; 548/361.1
See application file for complete search history.

(56) References Cited

FOREIGN PATENT DOCUMENTS

| WO | 2003/059899 A | 7/2003 |
|----|---------------|--------|
| WO | 2005/003098 A | 1/2005 |
| WO | 2005/030213 A | 4/2005 |
| WO | 2006/108699 A | 10/2006 |
| WO | 2007/046747 A | 4/2007 |

OTHER PUBLICATIONS van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*
Vippagunta SR, Brittain HG, and Grant D J, "Crystalline solids," Advanced Drug Delivery Reviews, May 2001,48(1), 3-26.*
Database Accession No. BRN: 223934 Abstract: Database Beilstein, Beilstein Institute for Organic Chemistry, Frankfurt-Main, DE, 1913.

* cited by examiner

*Primary Examiner* — San-ming Hui
*Assistant Examiner* — Paul Zarek
(74) *Attorney, Agent, or Firm* — Robert J. Smith

(57) ABSTRACT

The present invention provides compounds of formula (I):

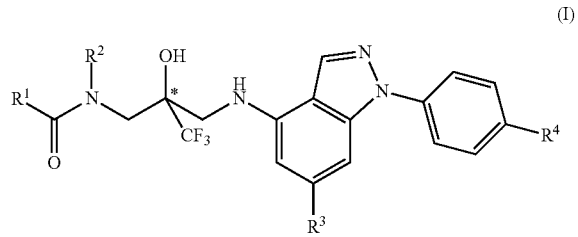

* = chiral centre a process for their preparation, pharmaceutical compositions comprising the compounds and the preparation of said compositions, intermediates and use of the compounds for the manufacture of a medicament for therapeutic treatment, particularly for the treatment of inflammation, allergy and/or skin disease.

10 Claims, No Drawings

COMPOUNDS

CROSS-REFERENCE TO RELATED APPLICATIONS

This application is filed pursuant to 35 U.S.C. §371 as a United States National Phase Application of International Application No. PCT/EP2007/060777 filed Oct. 10, 2007, which claims priority from GB0620385.5 filed Oct. 13, 2006 in the United Kingdom.

The present invention relates to non-steroidal compounds and a process for their preparation, to pharmaceutical compositions comprising the compounds and the preparation of said compositions, to intermediates and to use of the compounds for the manufacture of a medicament for therapeutic treatment, particularly for the treatment of inflammation and/or allergic conditions.

Nuclear receptors are a class of structurally related proteins involved in the regulation of gene expression. The steroid hormone receptors are a subset of this family whose natural ligands typically comprise endogenous steroids such as estradiol (estrogen receptor), progesterone (progesterone receptor) and cortisol (glucocorticoid receptor). Man-made ligands to these receptors play an important role in human health, in particular the use of glucocorticoid agonists to treat a wide range of inflammatory conditions.

Glucocorticoids exert their actions at the glucocorticoid receptor (GR) through at least two intracellular mechanisms, transactivation and transrepression (see: Schacke, H., Docke, W-D. & Asadullah, K. (2002) *Pharmacol and Therapeutics* 96:23-43; Ray, A., Siegel, M. D., Prefontaine, K. E. & Ray, P. (1995) *Chest* 107:139S; and Konig, H., Ponta, H., Rahmsdorf, H. J. & Herrlich, P. (1992) *EMBO J.* 11:2241-2246). Transactivation involves direct binding of the glucocorticoid receptor to distinct deoxyribonucleic acid (DNA) response elements (GREs) within gene promoters, usually but not always increasing the transcription of the downstream gene product. Recently, it has been shown that the GR can also regulate gene expression through an additional pathway (transrepression) in which the GR does not bind directly to DNA. This mechanism involves interaction of the GR with other transcription factors, in particular NFκB and AP1, leading to inhibition of their pro-transcriptional activity (Schacke, H., Docke, W-D. & Asadullah, K. (2002) *Pharmacol and Therapeutics* 96:23-43; and Ray, A., Siegel, M. D., Prefontaine, K. E. & Ray, P. (1995) *Chest* 107:139S). Many of the genes involved in the inflammatory response are transcriptionally activated through the NFκB and AP1 pathways and therefore inhibition of this pathway by glucocorticoids may explain their anti-inflammatory effect (see: Barnes, P. J. & Adcock, I. (1993) *Trend Pharmacol Sci* 14: 436-441; Cato, A. C. & Wade, E. (1996) *Bioessays* 18: 371-378).

Despite the effectiveness of glucocorticoids in treating a wide range of conditions, a number of side-effects are associated with pathological increases in endogenous cortisol or the use of exogenous, and particularly systemically administered, glucocorticoids. These include reduction in bone mineral density (Wong, C. A., Walsh, L. J., Smith, C. J. et al. (2000) *Lancet* 355:1399-1403), slowing of growth (Allen, D. B. (2000) *Allergy* 55: suppl 62, 15-18), skin bruising (Pauwels, R. A., Lofdahl, C. G., Latinen, L. A. et al. (1999) *N Engl J Med* 340:1948-1953), development of cataracts (Cumming, R. G., Mitchell, P. & Leeder, S. R. (1997) *N Engl J Med* 337:8-14) and dysregulation of lipid and glucose metabolism (Faul, J. L., Tormey, W., Tormey, V. & Burke, C. (1998) *BMJ* 317:1491; and Andrews, R. C. & Walker, B. R. (1999) *Clin Sci* 96:513-523). The side-effects are serious enough often to limit the dose of glucocorticoid that can be used to treat the underlying pathology leading to reduced efficacy of treatment.

Current known glucocorticoids have proved useful in the treatment of inflammation, tissue rejection, auto-immunity, various malignancies, such as leukemias and lymphomas, Cushing's syndrome, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia and Little's syndrome.

Glucocorticoids are especially useful in disease states involving systemic inflammation such as inflammatory bowel disease, systemic lupus erythematosus, polyarteritis nodosa, Wegener's granulomatosis, giant cell arteritis, rheumatoid arthritis, osteoarthritis, seasonal rhinitis, allergic rhinitis, vasomotor rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis and cirrhosis. Glucocorticoids have also been used as immunostimulants and repressors and as wound healing and tissue repair agents.

Glucocorticoids have also found use in the treatment of diseases such as inflammatory scalp alopecia, panniculitis, psoriasis, discoid lupus erythemnatosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform and cutaneous T-cell lymphoma.

The present invention provides compounds of formula (I):

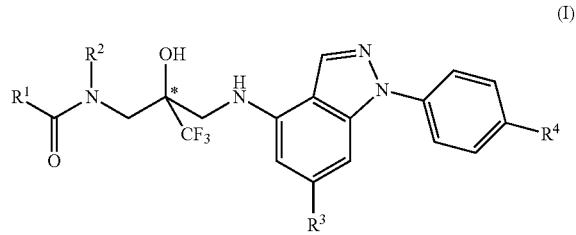

* = chiral centre wherein
$R^1$ is thienyl or

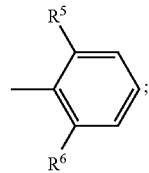

$R^2$ is ethyl or n-propyl;
$R^3$ is hydrogen or methyl;
$R^4$ is hydrogen or fluorine;
$R^5$ and $R^6$ are each independently hydrogen, methyl, fluorine, chlorine or trifluoromethyl; and salts thereof (hereinafter "compounds of the invention").

The compounds of the invention may provide agonism of the glucocorticoid receptor.

The compounds of formula (I) each contain a chiral centre and there are two possible stereoisomers (enantiomers) of each compound of formula (I). Further, at least one of the possible enantiomers of each compound of formula (I) modulates the glucocorticoid receptor.

The terms Enantiomer 1 and Enantiomer 2 are used herein to refer to the enantiomers of a compound of formula (I), based on the order of their elution using the chiral chromatography methodology described herein. Enantiomer 1 refers to the first enantiomer to elute, and Enantiomer 2 refers to the second enantiomer to elute.

It will be appreciated by those skilled in the art that although the absolute retention time on chromatography can be variable, the order of elution remains the same when the same column and conditions are employed. However, the use of a different chromatography column and conditions may alter the order of elution.

It will further be appreciated by those skilled in the art that at least one isomer (e.g. one enantiomer of the racemate) has the described activity. The other isomers may have similar activity, less activity, no activity or may have some antagonist activity in a functional assay.

In one embodiment of the invention the compound of formula (I) is a mixture of enantiomers, such as a racemic mixture. Thus, in one embodiment of the invention the compound of formula (I) is the racemic mixture (the racemate). In another embodiment of the invention the compound of formula (I) is a single enantiomer. Thus, in one embodiment of the invention the compound of formula (I) is Enantiomer 1. In a further embodiment of the invention the compound of formula (I) is Enantiomer 2.

It will be appreciated by those skilled in the art that as rotation of the aryl-carbonyl bond becomes less facile due to ortho substitution on the aromatic ring, atropisomerism may be observed thus creating the possibility of four isomers Enantiomer 1, Atropisomer 1; Enantiomer 1, Atropisomer 2; Enantiomer 2, Atropisomer 1; and Enantiomer 2, Atropisomer 2. Where the atropisomers are separated without separation of the enantiomers at the fixed chiral centre these are referred to a racemic atropisomers 1 and 2. Any comment relating to the biological activity of an isomer or stereoisomer should be taken to include these atropisomers. It will be appreciated by those skilled in the art that where there is a non equilibrium ratio of atropisomers, this ratio may move towards the equilibrium ratio.

In one embodiment, $R^1$ is 2-thienyl or 3-thienyl, for example 2-thienyl. In a further embodiment, $R^1$ is

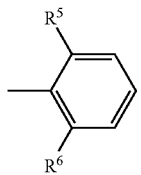

In one embodiment, $R^2$ is ethyl. In a further embodiment, $R^2$ is n-propyl.

In one embodiment, $R^3$ is hydrogen. In a further embodiment, $R^3$ is methyl;

In one embodiment, $R^4$ is hydrogen. In a further embodiment, $R^4$ is fluorine.

In one embodiment, $R^5$ and $R^6$ are both hydrogen, both methyl, both fluorine or both chlorine; $R^5$ is hydrogen and $R^6$ is methyl, fluorine or chlorine; $R^5$ is hydrogen and $R^6$ is methyl or fluorine; $R^5$ is methyl and $R^6$ is chlorine; or $R^5$ is fluorine and $R^6$ is chlorine or trifluoromethyl.

In another embodiment, $R^5$ and $R^6$ are both fluorine or both chlorine; or $R^5$ is hydrogen and $R^6$ is fluorine or chlorine.

In another embodiment, $R^5$ is hydrogen and $R^6$ is methyl.
In another embodiment, $R^5$ is hydrogen and $R^6$ is fluorine.
In a further embodiment, $R^5$ and $R^6$ are both chlorine.

It is to be understood that the present invention encompasses all combinations of the substituent groups described above.

In one embodiment the present invention provides compounds of formula (I)

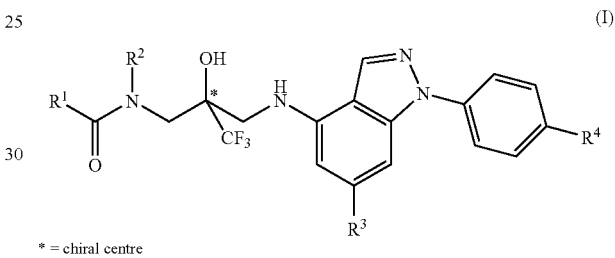

* = chiral centre wherein
$R^1$ is

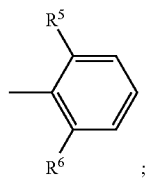

$R^2$ is ethyl;
$R^3$ is hydrogen;
$R^4$ is fluorine;
$R^5$ is hydrogen and $R^6$ is methyl, $R^5$ is hydrogen and $R^6$ is fluorine, or $R^5$ and $R^6$ are both chlorine; and
salts thereof.

In one embodiment, the compound of formula (I) is:
N-ethyl-N-(3,3,3-trifluoro-2-hydroxy-2-{[(1-phenyl-1H-indazol-4-yl)amino]methyl}propyl)benzamide;
N-ethyl-2-methyl-N-(3,3,3-trifluoro-2-hydroxy-2-{[(1-phenyl-1H-indazol-4-yl)amino]methyl}propyl)benzamide;
N-ethyl-2-fluoro-N-(3,3,3-trifluoro-2-hydroxy-2-{[(1-phenyl-1H-indazol-4-yl)amino]methyl}propyl)benzamide;
N-ethyl-2-fluoro-N-(3,3,3-trifluoro-2-hydroxy-2-{[(1-phenyl-1H-indazol-4-yl)amino]methyl}propyl)benzamide Enantiomer 1;
N-ethyl-2-fluoro-N-(3,3,3-trifluoro-2-hydroxy-2-{[(1-phenyl-1H-indazol-4-yl)amino]methyl}propyl)benzamide Enantiomer 2;

2-chloro-N-ethyl-N-(3,3,3-trifluoro-2-hydroxy-2-{[(1-phenyl-1H-indazol-4-yl)amino]methyl}propyl)benzamide;
N-ethyl-N-[3,3,3-trifluoro-2-({[1-(4-fluorophenyl)-1H-indazol-4-yl]amino}methyl)-2-hydroxypropyl]benzamide;
N-ethyl-2-methyl-N-[3,3,3-trifluoro-2-({[1-(4-fluorophenyl)-1H-indazol-4-yl]amino}methyl)-2-hydroxypropyl]benzamide;
N-ethyl-2-methyl-N-[3,3,3-trifluoro-2-({[1-(4-fluorophenyl)-1H-indazol-4-yl]amino}methyl)-2-hydroxypropyl]benzamide Enantiomer 1;
N-ethyl-2-methyl-N-[3,3,3-trifluoro-2-({[1-(4-fluorophenyl)-1H-indazol-4-yl]amino}methyl)-2-hydroxypropyl]benzamide Enantiomer 2;
N-ethyl-2-fluoro-N-[3,3,3-trifluoro-2-({[1-(4-fluorophenyl)-1H-indazol-4-yl]amino}methyl)-2-hydroxypropyl]benzamide;
N-ethyl-2-fluoro-N-[3,3,3-trifluoro-2-({[1-(4-fluorophenyl)-1H-indazol-4-yl]amino}methyl)-2-hydroxypropyl]benzamide Enantiomer 1;
N-ethyl-2-fluoro-N-[3,3,3-trifluoro-2-({[1-(4-fluorophenyl)-1H-indazol-4-yl]amino}methyl)-2-hydroxypropyl]benzamide Enantiomer 2;
2-chloro-N-ethyl-N-[3,3,3-trifluoro-2-({[1-(4-fluorophenyl)-1H-indazol-4-yl]amino}methyl)-2-hydroxypropyl]benzamide;
2-methyl-N-propyl-N-[3,3,3-trifluoro-2-({[1-(4-fluorophenyl)-1H-indazol-4-yl]amino}methyl)-2-hydroxypropyl]benzamide;
2-fluoro-N-propyl-N-[3,3,3-trifluoro-2-({[1-(4-fluorophenyl)-1H-indazol-4-yl]amino}methyl)-2-hydroxypropyl]benzamide;
N-ethyl-2-methyl-N-(3,3,3-trifluoro-2-hydroxy-2-{[(6-methyl-1-phenyl-1H-indazol-4-yl)amino]methyl}propyl)benzamide;
N-ethyl-2-fluoro-N-(3,3,3-trifluoro-2-hydroxy-2-{[(6-methyl-1-phenyl-1H-indazol-4-yl)amino]methyl}propyl)benzamide;
N-ethyl-N-(3,3,3-trifluoro-2-hydroxy-2-{[(6-methyl-1-phenyl-1H-indazol-4-yl)amino]methyl}propyl)-3-thiophenecarboxamide;
2-methyl-N-propyl-N-(3,3,3-trifluoro-2-hydroxy-2-{[(6-methyl-1-phenyl-1H-indazol-4-yl)amino]methyl}propyl)benzamide;
2-fluoro-N-propyl-N-(3,3,3-trifluoro-2-hydroxy-2-{[(6-methyl-1-phenyl-1H-indazol-4-yl)amino]methyl}propyl)benzamide;
N-ethyl-N-[3,3,3-trifluoro-2-({[1-(4-fluorophenyl)-6-methyl-1H-indazol-4-yl]amino}methyl)-2-hydroxypropyl]benzamide;
N-ethyl-2-methyl-N-[3,3,3-trifluoro-2-({[1-(4-fluorophenyl)-6-methyl-1H-indazol-4-yl]amino}methyl)-2-hydroxypropyl]benzamide;
N-ethyl-2-fluoro-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-N-[3,3,3-trifluoro-2-({[1-(4-fluorophenyl)-6-methyl-1H-indazol-4-yl]amino}methyl)-2-hydroxypropyl]benzamide;
N-ethyl-N-[3,3,3-trifluoro-2-({[1-(4-fluorophenyl)-6-methyl-1H-indazol-4-yl]amino}methyl)-2-hydroxypropyl]-2-thiophenecarboxamide;
N-ethyl-N-[3,3,3-trifluoro-2-({[1-(4-fluorophenyl)-6-methyl-1H-indazol-4-yl]amino}methyl)-2-hydroxypropyl]-3-thiophenecarboxamide;
N-propyl-N-[3,3,3-trifluoro-2-({[1-(4-fluorophenyl)-6-methyl-1H-indazol-4-yl]amino}methyl)-2-hydroxypropyl]benzamide;
2-methyl-N-propyl-N-[3,3,3-trifluoro-2-({[1-(4-fluorophenyl)-6-methyl-1H-indazol-4-yl]amino}methyl)-2-hydroxypropyl]benzamide;
2-fluoro-N-propyl-N-[3,3,3-trifluoro-2-({[1-(4-fluorophenyl)-6-methyl-1H-indazol-4-yl]amino}methyl)-2-hydroxypropyl]benzamide;
2-chloro-N-propyl-N-[3,3,3-trifluoro-2-({[1-(4-fluorophenyl)-6-methyl-1H-indazol-4-yl]amino}methyl)-2-hydroxypropyl]benzamide;
N-propyl-N-[3,3,3-trifluoro-2-({[1-(4-fluorophenyl)-6-methyl-1H-indazol-4-yl]amino}methyl)-2-hydroxypropyl]-2-thiophenecarboxamide;
N-propyl-N-[3,3,3-trifluoro-2-({[1-(4-fluorophenyl)-6-methyl-1H-indazol-4-yl]amino}methyl)-2-hydroxypropyl]-3-thiophenecarboxamide;
N-ethyl-N-(3,3,3-trifluoro-2-hydroxy-2-{[(6-methyl-1-phenyl-1H-indazol-4-yl)amino]methyl}propyl)benzamide;
2-chloro-N-ethyl-N-(3,3,3-trifluoro-2-hydroxy-2-{[(6-methyl-1-phenyl-1H-indazol-4-yl)amino]methyl}propyl)benzamide;
N-ethyl-N-(3,3,3-trifluoro-2-hydroxy-2-{[(1-phenyl-1H-indazol-4-yl)amino]methyl}propyl)-2-thiophenecarboxamide;
N-ethyl-N-(3,3,3-trifluoro-2-hydroxy-2-{[(1-phenyl-1H-indazol-4-yl)amino]methyl}propyl)-3-thiophenecarboxamide;
N-propyl-N-(3,3,3-trifluoro-2-hydroxy-2-{[(1-phenyl-1H-indazol-4-yl)amino]methyl}propyl)benzamide;
2-methyl-N-propyl-N-(3,3,3-trifluoro-2-hydroxy-2-{[(1-phenyl-1H-indazol-4-yl)amino]methyl}propyl)benzamide;
2-fluoro-N-propyl-N-(3,3,3-trifluoro-2-hydroxy-2-{[(1-phenyl-1H-indazol-4-yl)amino]methyl}propyl)benzamide;
2-chloro-N-propyl-N-(3,3,3-trifluoro-2-hydroxy-2-{[(1-phenyl-1H-indazol-4-yl)amino]methyl}propyl)benzamide;
N-propyl-N-(3,3,3-trifluoro-2-hydroxy-2-{[(1-phenyl-1H-indazol-4-yl)amino]methyl}propyl)-2-thiophenecarboxamide;
N-propyl-N-(3,3,3-trifluoro-2-hydroxy-2-{[(1-phenyl-1H-indazol-4-yl)amino]methyl}propyl)-3-thiophenecarboxamide;
N-ethyl-N-[3,3,3-trifluoro-2-({[1-(4-fluorophenyl)-1H-indazol-4-yl]amino}methyl)-2-hydroxypropyl]-2-thiophenecarboxamide;
N-ethyl-N-[3,3,3-trifluoro-2-({[1-(4-fluorophenyl)-1H-indazol-4-yl]amino}methyl)-2-hydroxypropyl]-3-thiophenecarboxamide;
N-propyl-N-[3,3,3-trifluoro-2-({[1-(4-fluorophenyl)-1H-indazol-4-yl]amino}methyl)-2-hydroxypropyl]benzamide;
2-chloro-N-propyl-N-[3,3,3-trifluoro-2-({[1-(4-fluorophenyl)-1H-indazol-4-yl]amino}methyl)-2-hydroxypropyl]benzamide;
N-propyl-N-[3,3,3-trifluoro-2-({[1-(4-fluorophenyl)-1H-indazol-4-yl]amino}methyl)-2-hydroxypropyl]-2-thiophenecarboxamide;
N-propyl-N-[3,3,3-trifluoro-2-({[1-(4-fluorophenyl)-1H-indazol-4-yl]amino}methyl)-2-hydroxypropyl]-3-thiophenecarboxamide;
N-ethyl-N-(3,3,3-trifluoro-2-hydroxy-2-{[(6-methyl-1-phenyl-1H-indazol-4-yl)amino]methyl}propyl)-2-thiophenecarboxamide;
N-propyl-N-(3,3,3-trifluoro-2-hydroxy-2-{[(6-methyl-1-phenyl-1H-indazol-4-yl)amino]methyl}propyl)benzamide;

N-propyl-N-(3,3,3-trifluoro-2-hydroxy-2-{[(6-methyl-1-phenyl-1H-indazol-4-yl)amino]methyl}propyl)-2-thiophenecarboxamide;
N-propyl-N-(3,3,3-trifluoro-2-hydroxy-2-{[(6-methyl-1-phenyl-1H-indazol-4-yl)amino]methyl}propyl)-3-thiophenecarboxamide;
N-ethyl-2,6-dimethyl-N-[3,3,3-trifluoro-2-({[1-(4-fluorophenyl)-1H-indazol-4-yl]amino}methyl)-2-hydroxypropyl]benzamide;
N-ethyl-2,6-dimethyl-N-[3,3,3-trifluoro-2-({[1-(4-fluorophenyl)-6-methyl-1H-indazol-4-yl]amino}methyl)-2-hydroxypropyl]benzamide;
N-ethyl-2,6-difluoro-N-[3,3,3-trifluoro-2-({[1-(4-fluorophenyl)-1H-indazol-4-yl]amino}methyl)-2-hydroxypropyl]benzamide;
N-ethyl-2,6-difluoro-N-[3,3,3-trifluoro-2-({[1-(4-fluorophenyl)-6-methyl-1H-indazol-4-yl]amino}methyl)-2-hydroxypropyl]benzamide;
2,6-dichloro-N-ethyl-N-[3,3,3-trifluoro-2-({[1-(4-fluorophenyl)-1H-indazol-4-yl]amino}methyl)-2-hydroxypropyl]benzamide;
2,6-dichloro-N-ethyl-N-[3,3,3-trifluoro-2-({[1-(4-fluorophenyl)-1H-indazol-4-yl]amino}methyl)-2-hydroxypropyl]benzamide Enantiomer 1;
2,6-dichloro-N-ethyl-N-[3,3,3-trifluoro-2-({[1-(4-fluorophenyl)-1H-indazol-4-yl]amino}methyl)-2-hydroxypropyl]benzamide Enantiomer 2;
2,6-dichloro-N-ethyl-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-6-fluoro-N-[3,3,3-trifluoro-2-({[1-(4-fluorophenyl)-1H-indazol-4-yl]amino}methyl)-2-hydroxypropyl]benzamide;
2-chloro-N-ethyl-6-fluoro-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-6-methyl-N-[3,3,3-trifluoro-2-({[1-(4-fluorophenyl)-1H-indazol-4-yl]amino}methyl)-2-hydroxypropyl]benzamide;
2-chloro-N-ethyl-6-methyl-N-[3,3,3-trifluoro-2-({[1-(4-fluorophenyl)-1H-indazol-4-yl]amino}methyl)-2-hydroxypropyl]benzamide Atropisomer 1;
2-chloro-N-ethyl-6-methyl-N-[3,3,3-trifluoro-2-({[1-(4-fluorophenyl)-1H-indazol-4-yl]amino}methyl)-2-hydroxypropyl]benzamide Atropisomer 2;
2-chloro-N-ethyl-6-methyl-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-6-methyl-N-[3,3,3-trifluoro-2-({[1-(4-fluorophenyl)-6-methyl-1H-indazol-4-yl]amino}methyl)-2-hydroxypropyl]benzamide Atropisomer 1;
2-chloro-N-ethyl-6-methyl-N-[3,3,3-trifluoro-2-({[1-(4-fluorophenyl)-6-methyl-1H-indazol-4-yl]amino}methyl)-2-hydroxypropyl]benzamide Atropsiomer 2;
N-ethyl-2-fluoro-N-[3,3,3-trifluoro-2-({[1-(4-fluorophenyl)-1H-indazol-4-yl]amino}methyl)-2-hydroxypropyl]-6-(trifluoromethyl)benzamide;
N-ethyl-2-fluoro-N-[3,3,3-trifluoro-2-({[1-(4-fluorophenyl)-6-methyl-1H-indazol-4-yl]amino}methyl)-2-hydroxypropyl]-6-(trifluoromethyl)benzamide; or
a salt thereof.

In one embodiment, the compound of formula (I) is:
N-ethyl-N-(3,3,3-trifluoro-2-hydroxy-2-{[(1-phenyl-1H-indazol-4-yl)amino]methyl}propyl)benzamide;
N-ethyl-2-methyl-N-(3,3,3-trifluoro-2-hydroxy-2-{[(1-phenyl-1H-indazol-4-yl)amino]methyl}propyl)benzamide;
N-ethyl-2-fluoro-N-(3,3,3-trifluoro-2-hydroxy-2-{[(1-phenyl-1H-indazol-4-yl)amino]methyl}propyl)benzamide;
2-chloro-N-ethyl-N-(3,3,3-trifluoro-2-hydroxy-2-{[(1-phenyl-1H-indazol-4-yl)amino]methyl}propyl)benzamide;
N-ethyl-N-[3,3,3-trifluoro-2-({[1-(4-fluorophenyl)-1H-indazol-4-yl]amino}methyl)-2-hydroxypropyl]benzamide;
N-ethyl-2-methyl-N-[3,3,3-trifluoro-2-({[1-(4-fluorophenyl)-1H-indazol-4-yl]amino}methyl)-2-hydroxypropyl]benzamide;
N-ethyl-2-fluoro-N-[3,3,3-trifluoro-2-({[1-(4-fluorophenyl)-1H-indazol-4-yl]amino}methyl)-2-hydroxypropyl]benzamide;
2-chloro-N-ethyl-N-[3,3,3-trifluoro-2-({[1-(4-fluorophenyl)-1H-indazol-4-yl]amino}methyl)-2-hydroxypropyl]benzamide;
2-methyl-N-propyl-N-[3,3,3-trifluoro-2-({[1-(4-fluorophenyl)-1H-indazol-4-yl]amino}methyl)-2-hydroxypropyl]benzamide;
2-fluoro-N-propyl-N-[3,3,3-trifluoro-2-({[1-(4-fluorophenyl)-1H-indazol-4-yl]amino}methyl)-2-hydroxypropyl]benzamide;
N-ethyl-2-methyl-N-(3,3,3-trifluoro-2-hydroxy-2-{[(6-methyl-1-phenyl-1H-indazol-4-yl)amino]methyl}propyl)benzamide;
N-ethyl-2-fluoro-N-(3,3,3-trifluoro-2-hydroxy-2-{[(6-methyl-1-phenyl-1H-indazol-4-yl)amino]methyl}propyl)benzamide;
N-ethyl-N-(3,3,3-trifluoro-2-hydroxy-2-{[(6-methyl-1-phenyl-1H-indazol-4-yl)amino]methyl}propyl)-3-thiophenecarboxamide;
2-methyl-N-propyl-N-(3,3,3-trifluoro-2-hydroxy-2-{[(6-methyl-1-phenyl-1H-indazol-4-yl)amino]methyl}propyl)benzamide;
2-fluoro-N-propyl-N-(3,3,3-trifluoro-2-hydroxy-2-{[(6-methyl-1-phenyl-1H-indazol-4-yl)amino]methyl}propyl)benzamide;
N-ethyl-N-[3,3,3-trifluoro-2-({[1-(4-fluorophenyl)-6-methyl-1H-indazol-4-yl]amino}methyl)-2-hydroxypropyl]benzamide;
N-ethyl-2-methyl-N-[3,3,3-trifluoro-2-({[1-(4-fluorophenyl)-6-methyl-1H-indazol-4-yl]amino}methyl)-2-hydroxypropyl]benzamide;
N-ethyl-2-fluoro-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-N-[3,3,3-trifluoro-2-({[1-(4-fluorophenyl)-6-methyl-1H-indazol-4-yl]amino}methyl)-2-hydroxypropyl]benzamide;
N-ethyl-N-[3,3,3-trifluoro-2-({[1-(4-fluorophenyl)-6-methyl-1H-indazol-4-yl]amino}methyl)-2-hydroxypropyl]-2-thiophenecarboxamide;
N-ethyl-N-[3,3,3-trifluoro-2-({[1-(4-fluorophenyl)-6-methyl-1H-indazol-4-yl]amino}methyl)-2-hydroxypropyl]-3-thiophenecarboxamide;
N-propyl-N-[3,3,3-trifluoro-2-({[1-(4-fluorophenyl)-6-methyl-1H-indazol-4-yl]amino}methyl)-2-hydroxypropyl]benzamide;
2-methyl-N-propyl-N-[3,3,3-trifluoro-2-({[1-(4-fluorophenyl)-6-methyl-1H-indazol-4-yl]amino}methyl)-2-hydroxypropyl]benzamide;
2-fluoro-N-propyl-N-[3,3,3-trifluoro-2-({[1-(4-fluorophenyl)-6-methyl-1H-indazol-4-yl]amino}methyl)-2-hydroxypropyl]benzamide;
2-chloro-N-propyl-N-[3,3,3-trifluoro-2-({[1-(4-fluorophenyl)-6-methyl-1H-indazol-4-yl]amino}methyl)-2-hydroxypropyl]benzamide;

N-propyl-N-[3,3,3-trifluoro-2-({[1-(4-fluorophenyl)-6-methyl-1H-indazol-4-yl]amino}methyl)-2-hydroxypropyl]-2-thiophenecarboxamide;
N-propyl-N-[3,3,3-trifluoro-2-({[1-(4-fluorophenyl)-6-methyl-1H-indazol-4-yl]amino}methyl)-2-hydroxypropyl]-3-thiophenecarboxamide;
N-ethyl-N-(3,3,3-trifluoro-2-hydroxy-2-{[(6-methyl-1-phenyl-1H-indazol-4-yl)amino]methyl}propyl)benzamide;
2-chloro-N-ethyl-N-(3,3,3-trifluoro-2-hydroxy-2-{[(6-methyl-1-phenyl-1H-indazol-4-yl)amino]methyl}propyl)benzamide;
N-ethyl-N-(3,3,3-trifluoro-2-hydroxy-2-{[(1-phenyl-1H-indazol-4-yl)amino]methyl}propyl)-2-thiophenecarboxamide;
N-ethyl-N-(3,3,3-trifluoro-2-hydroxy-2-{[(1-phenyl-1H-indazol-4-yl)amino]methyl}propyl)-3-thiophenecarboxamide;
N-propyl-N-(3,3,3-trifluoro-2-hydroxy-2-{[(1-phenyl-1H-indazol-4-yl)amino]methyl}propyl)benzamide;
2-methyl-N-propyl-N-(3,3,3-trifluoro-2-hydroxy-2-{[(1-phenyl-1H-indazol-4-yl)amino]methyl}propyl)benzamide;
2-fluoro-N-propyl-N-(3,3,3-trifluoro-2-hydroxy-2-{[(1-phenyl-1H-indazol-4-yl)amino]methyl}propyl)benzamide;
2-chloro-N-propyl-N-(3,3,3-trifluoro-2-hydroxy-2-{[(1-phenyl-1H-indazol-4-yl)amino]methyl}propyl)benzamide;
N-propyl-N-(3,3,3-trifluoro-2-hydroxy-2-{[(1-phenyl-1H-indazol-4-yl)amino]methyl}propyl)-2-thiophenecarboxamide;
N-propyl-N-(3,3,3-trifluoro-2-hydroxy-2-{[(1-phenyl-1H-indazol-4-yl)amino]methyl}propyl)-3-thiophenecarboxamide;
N-ethyl-N-[3,3,3-trifluoro-2-({[1-(4-fluorophenyl)-1H-indazol-4-yl]amino}methyl)-2-hydroxypropyl]-2-thiophenecarboxamide;
N-ethyl-N-[3,3,3-trifluoro-2-({[1-(4-fluorophenyl)-1H-indazol-4-yl]amino}methyl)-2-hydroxypropyl]-3-thiophenecarboxamide;
N-propyl-N-[3,3,3-trifluoro-2-({[1-(4-fluorophenyl)-1H-indazol-4-yl]amino}methyl)-2-hydroxypropyl]benzamide;
2-chloro-N-propyl-N-[3,3,3-trifluoro-2-({[1-(4-fluorophenyl)-1H-indazol-4-yl]amino}methyl)-2-hydroxypropyl]benzamide;
N-propyl-N-[3,3,3-trifluoro-2-({[1-(4-fluorophenyl)-1H-indazol-4-yl]amino}methyl)-2-hydroxypropyl]-2-thiophenecarboxamide;
N-propyl-N-[3,3,3-trifluoro-2-({[1-(4-fluorophenyl)-1H-indazol-4-yl]amino}methyl)-2-hydroxypropyl]-3-thiophenecarboxamide;
N-ethyl-N-(3,3,3-trifluoro-2-hydroxy-2-{[(6-methyl-1-phenyl-1H-indazol-4-yl)amino]methyl}propyl)-2-thiophenecarboxamide;
N-propyl-N-(3,3,3-trifluoro-2-hydroxy-2-{[(6-methyl-1-phenyl-1H-indazol-4-yl)amino]methyl}propyl)benzamide;
N-propyl-N-(3,3,3-trifluoro-2-hydroxy-2-{[(6-methyl-1-phenyl-1H-indazol-4-yl)amino]methyl}propyl)-2-thiophenecarboxamide;
N-propyl-N-(3,3,3-trifluoro-2-hydroxy-2-{[(6-methyl-1-phenyl-1H-indazol-4-yl)amino]methyl}propyl)-3-thiophenecarboxamide;
N-ethyl-2,6-dimethyl-N-[3,3,3-trifluoro-2-({[1-(4-fluorophenyl)-1H-indazol-4-yl]amino}methyl)-2-hydroxypropyl]benzamide;
N-ethyl-2,6-dimethyl-N-[3,3,3-trifluoro-2-({[1-(4-fluorophenyl)-6-methyl-1H-indazol-4-yl]amino}methyl)-2-hydroxypropyl]benzamide;
N-ethyl-2,6-difluoro-N-[3,3,3-trifluoro-2-({[1-(4-fluorophenyl)-1H-indazol-4-yl]amino}methyl)-2-hydroxypropyl]benzamide;
N-ethyl-2,6-difluoro-N-[3,3,3-trifluoro-2-({[1-(4-fluorophenyl)-6-methyl-1H-indazol-4-yl]amino}methyl)-2-hydroxypropyl]benzamide;
2,6-dichloro-N-ethyl-N-[3,3,3-trifluoro-2-({[1-(4-fluorophenyl)-1H-indazol-4-yl]amino}methyl)-2-hydroxypropyl]benzamide;
2,6-dichloro-N-ethyl-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-6-fluoro-N-[3,3,3-trifluoro-2-({[1-(4-fluorophenyl)-1H-indazol-4-yl]amino}methyl)-2-hydroxypropyl]benzamide;
2-chloro-N-ethyl-6-fluoro-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-6-methyl-N-[3,3,3-trifluoro-2-({[1-(4-fluorophenyl)-1H-indazol-4-yl]amino}methyl)-2-hydroxypropyl]benzamide;
2-chloro-N-ethyl-6-methyl-N-[3,3,3-trifluoro-2-({[1-(4-fluorophenyl)-6-methyl-1H-indazol-4-yl]amino}methyl)-2-hydroxypropyl]benzamide;
N-ethyl-2-fluoro-N-[3,3,3-trifluoro-2-({[1-(4-fluorophenyl)-1H-indazol-4-yl]amino}methyl)-2-hydroxypropyl]-6-(trifluoromethyl)benzamide;
N-ethyl-2-fluoro-N-[3,3,3-trifluoro-2-({[1-(4-fluorophenyl)-6-methyl-1H-indazol-4-yl]amino}methyl)-2-hydroxypropyl]-6-(trifluoromethyl)benzamide; or
a salt thereof.

In another embodiment, the compound of formula (I) is:
N-ethyl-2-fluoro-N-(3,3,3-trifluoro-2-hydroxy-2-{[(1-phenyl-1H-indazol-4-yl)amino]methyl}propyl)benzamide;
N-ethyl-2-fluoro-N-(3,3,3-trifluoro-2-hydroxy-2-{[(1-phenyl-1H-indazol-4-yl)amino]methyl}propyl)benzamide Enantiomer 1;
N-ethyl-2-methyl-N-[3,3,3-trifluoro-2-({[1-(4-fluorophenyl)-1H-indazol-4-yl]amino}methyl)-2-hydroxypropyl]benzamide Enantiomer 1;
N-ethyl-2-fluoro-N-[3,3,3-trifluoro-2-({[1-(4-fluorophenyl)-1H-indazol-4-yl]amino}methyl)-2-hydroxypropyl]benzamide;
N-ethyl-2-fluoro-N-[3,3,3-trifluoro-2-({[1-(4-fluorophenyl)-1H-indazol-4-yl]amino}methyl)-2-hydroxypropyl]benzamide Enantiomer 1;
2-chloro-N-ethyl-N-[3,3,3-trifluoro-2-({[1-(4-fluorophenyl)-1H-indazol-4-yl]amino}methyl)-2-hydroxypropyl]benzamide;
N-ethyl-2-fluoro-N-(3,3,3-trifluoro-2-hydroxy-2-{[(6-methyl-1-phenyl-1H-indazol-4-yl)amino]methyl}propyl)benzamide;
N-ethyl-N-[3,3,3-trifluoro-2-({[1-(4-fluorophenyl)-6-methyl-1H-indazol-4-yl]amino}methyl)-2-hydroxypropyl]benzamide;
N-ethyl-2-methyl-N-[3,3,3-trifluoro-2-({[1-(4-fluorophenyl)-6-methyl-1H-indazol-4-yl]amino}methyl)-2-hydroxypropyl]benzamide;
N-ethyl-2-fluoro-N-[3,3,3-trifluoro-2-({[1-(4-fluorophenyl)-6-methyl-1H-indazol-4-yl]amino}methyl)-2-hydroxypropyl]benzamide;
2-chloro-N-ethyl-N-[3,3,3-trifluoro-2-({[1-(4-fluorophenyl)-6-methyl-1H-indazol-4-yl]amino}methyl)-2-hydroxypropyl]benzamide;

N-ethyl-N-[3,3,3-trifluoro-2-({[1-(4-fluorophenyl)-6-methyl-1H-indazol-4-yl]amino}methyl)-2-hydroxypropyl]-2-thiophenecarboxamide;

2-methyl-N-propyl-N-[3,3,3-trifluoro-2-({[1-(4-fluorophenyl)-6-methyl-1H-indazol-4-yl]amino}methyl)-2-hydroxypropyl]benzamide;

2-fluoro-N-propyl-N-[3,3,3-trifluoro-2-({[1-(4-fluorophenyl)-6-methyl-1H-indazol-4-yl]amino}methyl)-2-hydroxypropyl]benzamide;

2-chloro-N-ethyl-N-(3,3,3-trifluoro-2-hydroxy-2-{[(6-methyl-1-phenyl-1H-indazol-4-yl)amino]methyl}propyl)benzamide;

N-ethyl-2,6-dimethyl-N-[3,3,3-trifluoro-2-({[1-(4-fluorophenyl)-6-methyl-1H-indazol-4-yl]amino}methyl)-2-hydroxypropyl]benzamide;

N-ethyl-2,6-difluoro-N-[3,3,3-trifluoro-2-({[1-(4-fluorophenyl)-1H-indazol-4-yl]amino}methyl)-2-hydroxypropyl]benzamide;

N-ethyl-2,6-difluoro-N-[3,3,3-trifluoro-2-({[1-(4-fluorophenyl)-6-methyl-1H-indazol-4-yl]amino}methyl)-2-hydroxypropyl]benzamide;

2,6-dichloro-N-ethyl-N-[3,3,3-trifluoro-2-({[1-(4-fluorophenyl)-1H-indazol-4-yl]amino}methyl)-2-hydroxypropyl]benzamide;

2,6-dichloro-N-ethyl-N-[3,3,3-trifluoro-2-({[1-(4-fluorophenyl)-1H-indazol-4-yl]amino}methyl)-2-hydroxypropyl]benzamide Enantiomer 1;

2,6-dichloro-N-ethyl-N-[3,3,3-trifluoro-2-({[1-(4-fluorophenyl)-6-methyl-1H-indazol-4-yl]amino}methyl)-2-hydroxypropyl]benzamide;

2-chloro-N-ethyl-6-fluoro-N-[3,3,3-trifluoro-2-({[1-(4-fluorophenyl)-1H-indazol-4-yl]amino}methyl)-2-hydroxypropyl]benzamide;

2-chloro-N-ethyl-6-fluoro-N-[3,3,3-trifluoro-2-({[1-(4-fluorophenyl)-6-methyl-1H-indazol-4-yl]amino}methyl)-2-hydroxypropyl]benzamide;

N-ethyl-2-fluoro-N-[3,3,3-trifluoro-2-({[1-(4-fluorophenyl)-1H-indazol-4-yl]amino}methyl)-2-hydroxypropyl]-6-(trifluoromethyl)benzamide;

N-ethyl-2-fluoro-N-[3,3,3-trifluoro-2-({[1-(4-fluorophenyl)-6-methyl-1H-indazol-4-yl]amino}methyl)-2-hydroxypropyl]-6-(trifluoromethyl)benzamide; or a salt thereof.

In another embodiment, the compound of formula (I) is:
N-ethyl-2-methyl-N-[3,3,3-trifluoro-2-({[1-(4-fluorophenyl)-1H-indazol-4-yl]amino}methyl)-2-hydroxypropyl]benzamide Enantiomer 1;

N-ethyl-2-fluoro-N-[3,3,3-trifluoro-2-({[1-(4-fluorophenyl)-1H-indazol-4-yl]amino}methyl)-2-hydroxypropyl]benzamide Enantiomer 1;

2,6-dichloro-N-ethyl-N-[3,3,3-trifluoro-2-({[1-(4-fluorophenyl)-1H-indazol-4-yl]amino}methyl)-2-hydroxypropyl]benzamide Enantiomer 1; or a salt thereof.

In another embodiment, the compound of formula (I) is:
N-ethyl-2-methyl-N-[3,3,3-trifluoro-2-({[1-(4-fluorophenyl)-1H-indazol-4-yl]amino}methyl)-2-hydroxypropyl]benzamide Enantiomer 1; or a salt thereof.

In another embodiment, the compound of formula (I) is:
N-ethyl-2-fluoro-N-[3,3,3-trifluoro-2-({[1-(4-fluorophenyl)-1H-indazol-4-yl]amino}methyl)-2-hydroxypropyl]benzamide Enantiomer 1; or a salt thereof.

In a further embodiment, the compound of formula (I) is:
2,6-dichloro-N-ethyl-N-[3,3,3-trifluoro-2-({[1-(4-fluorophenyl)-1H-indazol-4-yl]amino}methyl)-2-hydroxypropyl]benzamide Enantiomer 1; or a salt thereof.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or non crystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

One embodiment of the invention embraces compounds of formula (I) and salts and solvates thereof. Another embodiment of the invention embraces compounds of formula (I) and salts thereof. Another embodiment of the invention embraces compounds of formula (I) and solvates thereof. A further embodiment of the invention embraces compounds of formula (I) as the free base.

Salts and solvates of the compounds of formula (I) which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds of formula (I) and their pharmaceutically acceptable salts thereof.

Suitable salts according to the invention are those formed with bases. Pharmaceutically acceptable base salts include alkali metal salts such as those of sodium and potassium. Further pharmaceutically acceptable base salts include lithium, calcium, magnesium, aluminum and zinc salts; and carbonates and bicarbonates of a pharmaceutically acceptable metal cation such as sodium, potassium, lithium, calcium, magnesium, aluminum and zinc.

The compounds of formula (I) and pharmaceutically acceptable salts thereof are expected to have potentially beneficial anti-inflammatory or anti-allergic effects, particularly upon topical administration, demonstrated by, for example, their ability to bind to the glucocorticoid receptor and to illicit a response via that receptor. Hence, the compounds of formula (I) and pharmaceutically acceptable salts thereof may be of use in the treatment of inflammatory and/or allergic disorders.

Examples of disease states in which the compounds of formula (I) and pharmaceutically acceptable salts thereof are expected to have utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease (COPD), interstitial lung disease, and fibrosis; inflammatory bowel conditions such as ulcerative colitis and Crohn's disease; and auto-immune diseases such as rheumatoid arthritis.

The term "rhinitis" is used herein to refer to all types of rhinitis including allergic rhinitis such as seasonal rhinitis (for example hayfever) or perennial rhinitis, and non-allergic rhinitis or vasomotor rhinitis.

It will be appreciated by those skilled in the art that reference herein to treatment extends to prophylaxis as well as the treatment of established conditions.

As mentioned above, compounds of formula (I) and pharmaceutically acceptable salts thereof are expected to be of use in human or veterinary medicine, in particular as anti-inflammatory and/or anti-allergic agents.

There is thus provided as a further aspect of the invention a compound of formula (I) or a pharmaceutically acceptable salt thereof for use in human or veterinary medicine, particularly in the treatment of patients with inflammatory and/or allergic conditions, such as rheumatoid arthritis, asthma, COPD, allergy and/or rhinitis.

There is thus provided as a further aspect of the invention a compound of formula (I) or a pharmaceutically acceptable salt thereof for use in the treatment of patients with rhinitis.

Further provided is a compound of formula (I) or a pharmaceutically acceptable salt thereof for use in the treatment of patients with skin disease such as eczema, psoriasis, allergic dermatitis, neurodermatitis, pruritis and/or hypersensitivity reactions.

According to another aspect of the invention, there is provided the use of a compound of formula (I) or a pharmaceutically acceptable salt thereof for the manufacture of a medicament for the treatment of patients with inflammatory and/or allergic conditions, such as rheumatoid arthritis, asthma, COPD, allergy and/or rhinitis.

According to another aspect of the invention, there is provided the use of a compound of formula (I) or a pharmaceutically acceptable salt thereof for the manufacture of a medicament for the treatment of patients with rhinitis.

According to yet to another aspect of the invention, there is provided the use of a compound of formula (I) or a pharmaceutically acceptable salt thereof for the manufacture of a medicament for the treatment of patients with skin disease such as eczema, psoriasis, allergic dermatitis, neurodermatitis, pruritis and/or hypersensitivity reactions.

In a further or alternative aspect, there is provided a method for the treatment of a human or animal subject with an inflammatory and/or allergic condition such as rheumatoid arthritis, asthma, COPD, allergy and/or rhinitis, which method comprises administering to said human or animal subject an effective amount of a compound of formula (I) or a pharmaceutically acceptable salt thereof.

In a further or alternative aspect, there is provided a method for the treatment of a human or animal subject with rhinitis, which method comprises administering to said human or animal subject an effective amount of a compound of formula (I) or a pharmaceutically acceptable salt thereof.

In yet a further or alternative aspect, there is provided a method for the treatment of a human or animal subject with skin disease such as eczema, psoriasis, allergic dermatitis, neurodermatitis, pruritis and/or hypersensitivity reactions, which method comprises administering to said human or animal subject an effective amount of a compound of formula (I) or a pharmaceutically acceptable salt thereof.

The compounds of formula (I) and pharmaceutically acceptable salts thereof may be formulated for administration in any convenient way, and the invention therefore also includes within its scope pharmaceutical compositions comprising a compound of formula (I) or a pharmaceutically acceptable salt thereof together, if desirable, in admixture with one or more physiologically acceptable diluents or carriers.

Further, there is provided a process for the preparation of such pharmaceutical compositions which comprises mixing the ingredients. A pharmaceutical composition comprising a compound of formula (I) or a pharmaceutically acceptable salt thereof, may be prepared by, for example, admixture at ambient temperature and atmospheric pressure.

Pharmaceutical compositions comprising a compound of formula (I) or a pharmaceutically acceptable salt thereof may be suitable for topical administration (which includes epicutaneous, inhaled, intranasal or ocular administration), enteral administration (which includes oral or rectal administration) or parenteral administration (such as by injection or infusion). The compounds of formula (I) and pharmaceutically acceptable salts thereof may, for example, be formulated for oral, buccal, sublingual, parenteral, local rectal administration or other local administration.

Pharmaceutical compositions may be in the form of, for example, solutions or suspensions (aqueous or non-aqueous), tablet, capsules, oral liquid preparations, powders, granules, lozenges, lotions, creams, ointments, gels, foams, reconstitutable powders or suppositories as required by the route of administration.

Generally, compositions containing a compound of formula (I) or a pharmaceutically acceptable salt thereof may contain from about 0.1 to about 99%, such as from about 10 to about 60%, by weight based on the total weight of the composition, of the compound of formula (I) or a pharmaceutically acceptable salt thereof, depending on the route of administration. The dose of the compound used in the treatment of the abovementioned disorders will vary in the usual way with the seriousness of the disorders, the weight of the sufferer and other similar factors. However, as a general guide, suitable unit does may be about 0.001 to about 100 mg, for example about 0.001 to about 1 mg, and such unit doses may be administered more than once a day, for example two or three times a day. Such therapy may extend for a number of weeks or month.

The compounds of formula (I) and pharmaceutically acceptable salts thereof may, for example, be formulated for oral, buccal, sublingual, parenteral, local rectal administration or other local administration.

Local administration as used herein includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (for example eye or nose drops), solutions/suspensions for nebulisation, suppositories, pessaries, retention enemas and chewable or suckable tablets or pellets (for example for the treatment of aphthous ulcers) or liposome or microencapsulation preparations.

The proportion of the active compound of formula (I) or a pharmaceutically acceptable salt thereof in the local compositions according to the invention depends on the precise type of composition to be prepared, and the route of administration, but will generally be within the range of from 0.001 to 10% by weight based on the total weight of the composition. Generally, for most types of preparations, the proportion used will be within the range of from 0.005 to 1%, for example from 0.01 to 1%, such as 0.01 to 0.5% by weight based on the total weight of the composition. However, in powders for inhalation or insufflation the proportion used will normally be within the range of from 0.1 to 5% by weight based on the total weight of the composition.

In one embodiment, pharmaceutical compositions comprising a compound of formula (I) or a pharmaceutically acceptable salt thereof may be suitable for topical administration, for example for intranasal or inhaled administration. Inhaled administration involves topical administration to the lung, such as by aerosol or dry powder composition.

Generally, compositions suitable for intranasal or inhaled administration may conveniently be formulated as aerosols, solutions, suspensions, drops, gels or dry powders, optionally with one or more physiologically acceptable diluents and/or carriers such as aqueous or non-aqueous vehicles, thickening agents, isotonicity adjusting agents, antioxidants and/or preservatives.

For compositions suitable for intranasal or inhaled administration, the compound of formula (I) or a pharmaceutically acceptable salt thereof may be in a particle-size-reduced form prepared by, for example, micronisation and milling. Generally, the size-reduced (e.g. micronised) compound can be defined by a $D_{50}$ value of about 0.5 to about 10 microns (for example as measured using laser diffraction).

In one embodiment, pharmaceutical compositions comprising a compound of formula (I) or a pharmaceutically acceptable salt thereof are suitable for intranasal administration. For example, the compounds of formula (I) and pharmaceutically acceptable salts thereof may be formulated for intranasal use in man either as a solution composition or a suspension composition, for example as a solution composition such as an aqueous solution composition.

A suitable dosing regime for an intranasal composition may be for the patient to inhale slowly through the nose subsequent to the nasal cavity being cleared. During inhalation, the composition may be administered to one nostril while the other is manually compressed. This procedure may then be repeated for the other nostril. Generally, one or two sprays per nostril may be administered by the above procedure up to two or three times each day. In one embodiment, the intranasal compositions comprising a compound of formula (I) or a pharmaceutically acceptable salt thereof are suitable for once daily administration. Typically, each spray to the nostril may deliver from about 25 to about 100 µL of intranasal composition. Further, generally, each spray to the nostril may deliver from about 1 to about 100 µg, for example about 1 to about 50 µg, of the compound of formula (I) or a pharmaceutically acceptable salt thereof.

Intranasal compositions comprising a compound of formula (I) or a pharmaceutically acceptable salt thereof may permit the compound to be delivered to all areas of the nasal cavities (the target tissue) and further, may permit the compound to remain in contact with the target tissue for longer periods of time. Compositions comprising a compound of formula (I) or a pharmaceutically acceptable salt thereof, suitable for intranasal administration, may optionally contain one or more suspending agents, one or more preservatives, one or more wetting agents and/or one or more isotonicity adjusting agents as desired. Compositions suitable for intranasal administration may optionally further contain other excipients such as antioxidants (for example sodium metabisulphite), taste-masking agents (for example menthol) and sweetening agents (for example dextrose, glycerol, saccharin and/or sorbitol). Excipients that may be employed in intranasal compositions include, for example, xylitol, potassium sorbate, EDTA, sodium citrate, citric acid, polysorbate 80 and Avicel CL611.

The suspending agent, if included, will typically be present in the intranasal composition in an amount of between about 0.1 and 5%, such as between about 1.5 and 2.4%, by weight based on the total weight of the composition. Examples of suspending agents include Avicel, carboxymethylcellulose, veegum, tragacanth, bentonite, methylcellulose and polyethylene glycols, e.g. microcrystalline cellulose or carboxy methylcellulose sodium. Suspending agents may also be included in, for example, compositions suitable for inhaled, ocular and oral administration, as appropriate.

For stability purposes, intranasal compositions comprising a compound of formula (I) or a pharmaceutically acceptable salt thereof may be protected from microbial or fungal contamination and growth by inclusion of a preservative. Examples of pharmaceutically acceptable anti-microbial agents or preservatives may include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives may include sodium benzoate. In one embodiment, there is provided a pharmaceutical composition comprising a compound of formula (I) or a pharmaceutically acceptable salt thereof which is benzalkonium chloride-free. The preservative, if included, may be present in an amount of between about 0.001 and about 1%, such as about 0.015%, by weight based on the total weight of the composition. Preservatives may be included in composition suitable for other routes of administration as appropriate.

Compositions which contain a suspended medicament may include a pharmaceutically acceptable wetting agent which functions to wet the particles of the medicament to facilitate dispersion thereof in the aqueous phase of the composition. Typically, the amount of wetting agent used will not cause foaming of the dispersion during mixing. Examples of wetting agents include fatty alcohols, esters and ethers, such as polyoxyethylene (20) sorbitan monooleate (polysorbate 80). The wetting agent may be present in the composition in an amount of between about 0.001 and about 1%, for example between about 0.005% and about 1%, by weight based on the total weight of the composition. Wetting agents may be included in compositions suitable for other routes of administration, e.g. for inhaled or ocular administration, as appropriate.

An isotonicity adjusting agent may be included to achieve isotonicity with body fluids e.g. fluids of the nasal cavity, resulting in reduced levels of irritancy. Examples of isotonicity adjusting agents include sodium chloride, dextrose, xylitol and calcium chloride. An isotonicity agent may be included in the composition in an amount of between about 0.1 and 10%, such as about 4.5% by weight based on the total weight of the composition. Isotonicity adjusting agents may also be included in, for example, compositions suitable for inhaled, ocular, oral and parenteral forms of administration, as appropriate.

Further, intranasal compositions may be buffered by the addition of suitable buffering agents such as sodium citrate, citric acid, phosphates such as disodium phosphate (for example dodecahydrate, heptahydrate, dihydrate and anhydrous forms) or sodium phosphate and mixtures thereof. Buffering agents may also be included in compositions suitable for other routes of administration, as appropriate.

Compositions for administration topically to the nose for example, for the treatment of rhinitis, include pressurised aerosol compositions and aqueous compositions administered to the nose by pressurised pump. In one embodiment, the present invention encompasses compositions which are non-pressurised and adapted to be administered topically to the nasal cavity. Suitable compositions contain water as the diluent or carrier for this purpose. Aqueous compositions for administration to the lung or nose may be provided with conventional excipients such as buffering agents, tonicity modifying agents and the like. Aqueous compositions may also be administered to the nose by nebulisation.

The compounds of formula (I) and pharmaceutically acceptable salts thereof may be formulated as a fluid composition for delivery from a fluid dispenser, for example a fluid dispenser having a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid compositions. The housing has at least one finger-operable side lever which is movable inwardly with respect to the housing to cam the container upwardly in the housing to cause the pump to compress and pump a metered dose of the composition out of a pump stem through a nasal nozzle of the housing. In one embodiment, the fluid dispenser is of the general type illustrated in FIGS. 30-40 of WO05/044354.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants for example, oleic acid, lecithin or an oligolactic acid or derivative such as those described in WO94/21229 and WO98/34596 and cosolvents, for example ethanol.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon or mixtures thereof as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Aerosol compositions may be presented in single or multidose quantities in sterile form in a sealed container, which may take the form of a cartridge or refill for use with an atomising device or inhaler. Alternatively, the sealed container may be a unitary dispensing device such as a single dose nasal inhaler or an aerosol dispenser fitted with a metering valve (metered dose inhaler), which is intended for disposal once the contents of the container have been exhausted.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 µg to 10 mg of the compound of formula (I) or a pharmaceutically acceptable salt thereof. Alternatively, the compound of formula (I) or a pharmaceutically acceptable salt thereof may be presented without excipients such as lactose.

Optionally, in particular for dry powder inhalable compositions, a composition suitable for inhaled administration may be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition may be administered by inhalation via a device such as the DISKUS™ device, marketed by GlaxoSmithKline. The DISKUS™ inhalation device is, for example, described in GB2242134A, and in such a device, at least one container for the composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the composition in powder form from the opened container.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 µg to 10 mg, preferably from 20 µg to 2000 µg, more preferably from 20 µg to 500 µg of a compound of formula (I) or a pharmaceutically acceptable salt thereof. Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol formulations.

In the case of suspension aerosol formulations, the particle size of the particulate (for example, micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of a compound of formula (I) or a pharmaceutically acceptable salt thereof may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (for example, see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, most preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Topical preparations may be administered by one or more applications per day to the affected area; over skin areas occlusive dressings may advantageously be used. Continuous or prolonged delivery may be achieved by an adhesive reservoir system.

Ointments, creams (for example an oil-in-water or water-in-oil composition such as an emulsion) and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents. Topical preparations may also optionally contain one or more solubilising agents and/or skin penetration-enhancing agents and/or surfactants and/or fragrances and/or preservatives and/or emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

In one embodiment, there is provided a pharmaceutical composition comprising a compound of formula (I) or a pharmaceutically acceptable salt thereof which is suitable for ocular administration. Such compositions may optionally contain one or more suspending agents, one or more preservatives, one or more wetting/lubricating agents and/or one or more isotonicity adjusting agents. Examples of ophthalmic wetting/lubricating agents may include cellulose derivatives, dextran 70, gelatine, liquid polyols, polyvinyl alcohol and povidone such as cellulose derivatives and polyols.

For internal administration the compounds of formula (I) and pharmaceutically acceptable salts thereof may, for example, be formulated in conventional manner for oral, nasal, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms may be preferred as described below.

The compounds of formula (I) and pharmaceutically acceptable salts thereof may in general be given by internal administration in cases wherein systemic glucocorticoid receptor agonist therapy is indicated.

Slow release or enteric coated formulations may be advantageous, particularly for the treatment of inflammatory bowel disorders.

Fluid unit dosage forms for parenteral administration may be prepared using a compound of formula (I) or a pharmaceutically acceptable salt thereof and a sterile vehicle which may be aqueous or oil based. The compound of formula (I) or a pharmaceutically acceptable salt thereof, depending on the vehicle and concentration used, may be either suspended or dissolved in the vehicle. In preparing solutions, the compound of formula (I) or a pharmaceutically acceptable salt thereof may be dissolved for injection and filter sterilised before filling into a suitable vial or ampoule and sealing. Optionally, adjuvants such as a local anaesthetic, preservatives and buffering agents may be dissolved in the vehicle. To enhance the stability, the composition may be frozen after filling into the vial and the water removed under vacuum. The lyophilised parenteral composition may be reconstituted with a suitable solvent just prior to administration. Parenteral suspensions may be prepared in substantially the same manner, except that the compound is suspended in the vehicle instead of being dissolved, and sterilisation cannot be accomplished by filtration. The compound may be sterilised by exposure to ethylene oxide before suspension in a sterile vehicle. A surfactant or wetting agent may be included in the composition to facilitate uniform distribution of the compound.

In some embodiments, the compounds of formula (I) and pharmaceutically acceptable salts thereof may be formulated for oral administration. In other embodiments, the compounds of formula (I) and pharmaceutically acceptable salts thereof may be formulated for inhaled administration. In further embodiments, the compounds of formula (I) and pharmaceutically acceptable salts thereof may be formulated for intranasal administration.

The compounds and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer.

Other $\beta_2$-adrenoreceptor agonists include those described in WO02/066422, WO02/070490, WO02/076933, WO03/

024439, WO03/072539, WO03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:

3-(4-{[6-({(2R)-2-hydroxy-2-[4-hydroxy-3-(hydroxymethyl)phenyl]ethyl}amino) hexyl]oxy}butyl)benzenesulfonamide;

3-(3-{[7-({(2R)-2-hydroxy-2-[4-hydroxy-3-hydroxymethyl)phenyl]ethyl}-amino)heptyl]oxy}propyl)benzenesulfonamide;

4-{(1R)-2-[(6-{2-[(2,6-dichlorobenzyl)oxy]ethoxy}hexyl)amino]-1-hydroxyethyl}-2-(hydroxymethyl)phenol;

4-{(1R)-2-[(6-{4-[3-(cyclopentylsulfonyl)phenyl]butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Examples of corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydrofuran-3S-yl)ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxypregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those covered in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398, WO06/015870, WO06/108699, WO07/000,334 and WO07/054,294.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment the invention provides the use of the compounds of formula (I) or a pharmaceutically acceptable salt thereof in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as Cl-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd).

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
3-((endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide.
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I), or a pharmaceutically acceptable salt thereof, together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I), or a pharmaceutically acceptable salt thereof, together with an H3 antagonist (and/or inverse agonist). Examples of H3 antagonists include, for example, those compounds disclosed in WO2004/035556 and in WO2006/

045416. Other histamine receptor antagonists which may be used in combination with the compounds of formula (I), or a pharmaceutically acceptable salt thereof, include antagonists (and/or inverse agonists) of the H4 receptor, for example, the compounds disclosed in Jablonowski et al., *J. Med. Chem.* 46:3957-3960 (2003).

The invention thus provides, in another aspect, a combination comprising a compound of formula (I) or a pharmaceutically acceptable salt thereof together with a PDE4 inhibitor.

The invention thus provides, in another aspect, a combination comprising a compound of formula (I) or a pharmaceutically acceptable salt thereof together with a $\beta_2$-adrenoreceptor agonist.

The invention thus provides, in another aspect, a combination comprising a compound of formula (I) or a pharmaceutically acceptable salt thereof together with a corticosteroid.

The invention thus provides, in another aspect, a combination comprising a compound of formula (I) or a pharmaceutically acceptable salt thereof together with another non-steroidal GR agonist.

The invention thus provides, in another aspect, a combination comprising a compound of formula (I) or a pharmaceutically acceptable salt thereof together with an anticholinergic.

The invention thus provides, in another aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with another non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a compound of formula (I) or a pharmaceutically acceptable salt thereof together with an anticholinergic and a PDE4 inhibitor.

The present invention also provides a process for the preparation of compounds of formula (I) comprising acylation of an amine of formula (II)

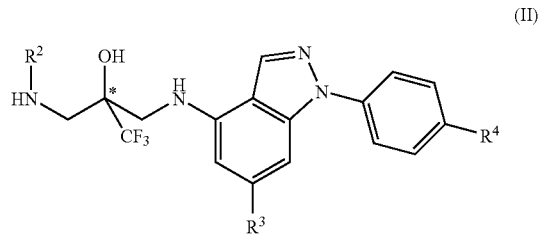

* = chiral centre wherein the groups $R^2$, $R^3$ and $R^4$ are as defined above for compounds of formula (I), with a carboxylic acid of formula (III) or an activated derivative thereof.

wherein $R^1$ is as defined above for compounds of formula (I).

Compounds of formula (III) are known and are commercially available from, for example, Aldrich.

Acylations using a carboxylic acid of formula (III) may be carried out in a conventional organic solvent, for example N,N-dimethylformamide, in the presence of a coupling agent such as those described in *Tetrahedron* 2005, 61, 10827, for example O-(7-azabenzotriazol-1-yl)-N,N,N',N'-tetramethyluronium hexafluorophosphate (HATU), and a base, for example triethylamine or N,N-diisopropylethylamine. The reaction may be carried out at a temperature from −10° C. to 100° C., for example at room temperature.

Alternatively the carboxylic acids of formula (III) may, for example, be activated as their acid chlorides which may then be reacted with an amine of formula (II) in a conventional organic solvent, for example dichloromethane, in the presence of a base, for example N,N-diisopropylethylamine. The reaction may be carried out at a temperature from −10° C. to 100° C., for example at room temperature.

Compounds of formula (II) may be prepared by reaction of an epoxide of formula (IV)

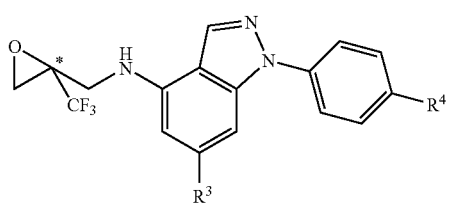

(IV)

* = chiral centre wherein the groups $R^3$ and $R^4$ are as defined above for compounds of formula (I), with either ethylamine or n-propylamine. The reaction may be carried out in a conventional organic solvent, for example acetonitrile or tetrahydrofuran, and at a temperature from −10° C. to 100° C., for example at room temperature.

Compounds of formula (IV) may be prepared by reaction of a 4-amino-1-arylindazole of formula (V)

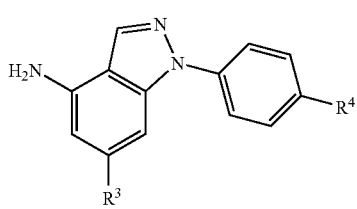

(V)

wherein the groups $R^3$ and $R^4$ are as defined above for compounds of formula (I), with the epoxy tosylate of formula (VI)

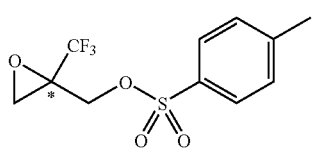

(VI)

* = chiral cetnre

The reaction of (V) with (VI) may be conducted for example in the presence of bismuth chloride or ytterbium triflate in dichloromethane or acetonitrile and gives, initially, the intermediate tosylate (VII) which may be isolated if required

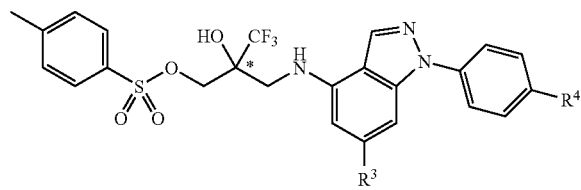

(VII)

* = chiral centre wherein the groups $R^3$ and $R^4$ are as defined above for compounds of formula (I).

Addition of tetrahydrofuran and polymer supported carbonate resin results in cyclisation of the tosylate (VII) to give the epoxide (IV).

Alternatively, compounds of formula (II) may be obtained by reaction of the intermediate tosylate (VII) with ethylamine of n-propylamine in dichloromethane.

The aminoindazoles of formula (V) may be prepared by reaction of a 1H-indazol-4-amine of formula (VIII):

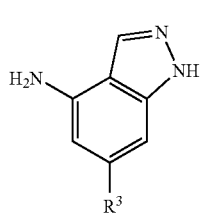

(VIII)

wherein $R^3$ is hydrogen or methyl, with iodobenzene or 1-fluoro-4-iodobenzene.

This N-arylation reaction may be performed in the presence of a copper(I) catalyst, such as copper(I) iodide and a weak base such as potassium carbonate or potassium phosphate and an amine ligand such as L-proline, cyclohexanediamine, N,N'-dimethylcyclohexanediamine or N,N'-dimethylethylenediamine in a variety of solvents including toluene, dioxane, N,N-dimethylformamide, N,N-dimethylacetamide and dimethylsulfoxide at a temperature in the range 60-160° C., most typically 110° C. Representative procedures are reported in the literature: *Synthesis* 2005, 3, 496-499, *J. Org. Chem.*, 2004, 69, 5578-5587 and *J. Am. Chem. Soc.*, 2001, 123, 7727-7729.

Alternatively compounds of formula (V) may be prepared by similar reaction of a 4-nitro-1H-indazole of formula (IX)

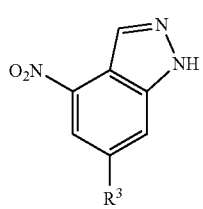

(IX)

wherein $R^3$ is hydrogen or methyl, with iodobenzene or 1-fluoro-4-iodobenzene followed by reduction of the nitro group by, for example, hydrogenation over palladium on carbon.

The amino and nitro indazoles of formulae (VIII) and (IX) have been described in the literature: *Journal of the Chemical Society*, 1955, 2412-2423 and references cited therein.

Alternatively the intermediate 4-nitro-1-arylindazoles of formula (X)

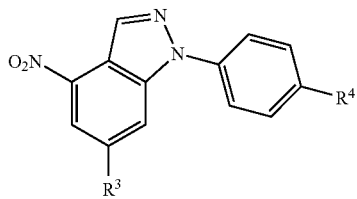
(X)

wherein the groups $R^3$ and $R^4$ are as defined above for compounds of formula (I), may be prepared by reaction of the corresponding 2,6-dinitro benzaldehydes of formula (XI)

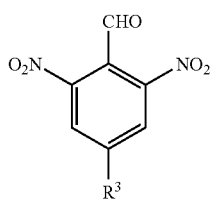
(XI)

wherein the group $R^3$ is hydrogen or methyl with phenylhydrazine or 4-fluorophenylhydrazine followed by base catalysed cyclisation of the intermediate phenylhydrazones using the methodology described in the literature: *Berichte*, 1925, 58B, 1369-1375.

Alternatively compounds of formula (V) may be prepared from the corresponding 4-bromo derivatives of formula (XII)

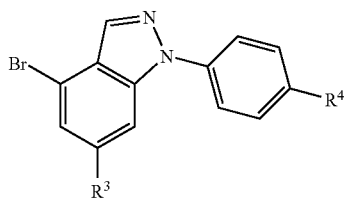
(XII)

wherein the groups $R^3$ and $R^4$ are as defined above for compounds of formula (I), by palladium catalysed amination with benzophenone imine followed by acid hydrolysis of the intermediate imines using methodology described by Wolfe in *Tetrahedron Letters*, 38, 6367-6370.

Compounds of formula (XII) may be prepared by cyclisation of hydrazones of formula (XIII)

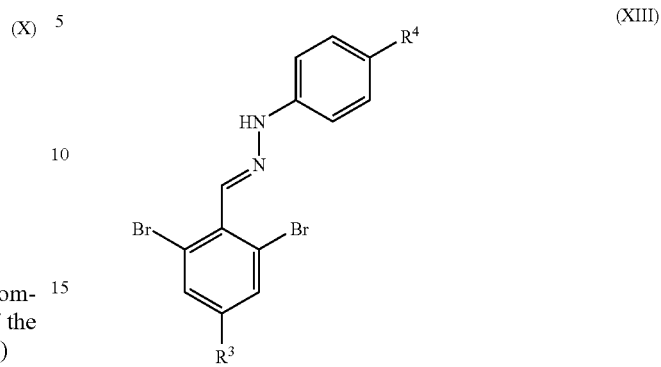
(XIII)

wherein the groups $R^3$ and $R^4$ are as defined above for compounds of formula (I). This intramolecular N-arylation may be conducted using palladium catalysis of the type described by Buchwald in *Topics in Current Chemistry*, 2002, 219, 131-209. For example, the cyclisation may be effected using tris(dibenzylideneacetone)dipalladium(0), racemic-BINAP (2,2'-bis(diphenylphosphino)-1,1'-binaphthyl) and tripotassium phosphate in toluene or 1,4-dioxane at reflux temperature.

Hydrazones of formula (XIII) may be prepared by reaction of an aldehyde of formula (XIV)

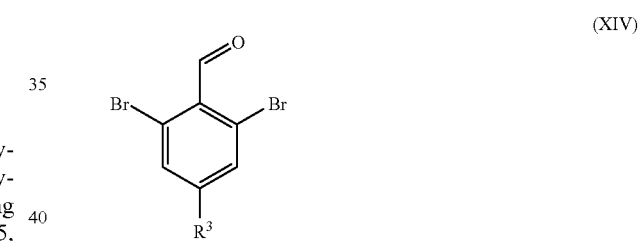
(XIV)

wherein $R^3$ is hydrogen or methyl, with phenyl hydrazine or 4-fluorophenylhydrazine. Aldehydes of formula (XII) are known and may be prepared as described by Lulinski and Serwatowski in *J. Org. Chem.*, 2003, 68, 5384-5387

Phenyl hydrazine and 4-fluorophenylhydrazine are commercially available from, for example, Aldrich.

The intermediate epoxy tosylate (VI) may be prepared by treating a compound of formula (XV)

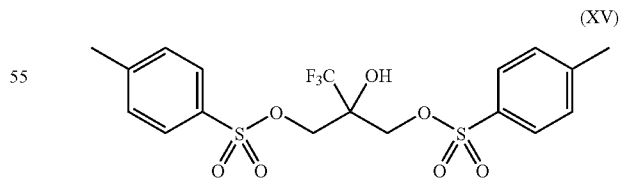
(XV)

with a polymer supported carbonate resin. The reaction may be carried out in a conventional organic solvent, for example dichloromethane and may be conducted using either a batch or a flow process. The reaction may be carried out at a temperature from −10° C. to 100° C., for example at room temperature for a batch process or at about 50° C. for a flow process.

Compound (XV) may be prepared by treating the triol (XVI)

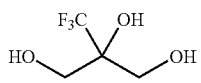
(XVI)

with 4-methylbenzenesulphonyl chloride in the presence of an organic base, for example pyridine. The reaction may be carried out at a temperature of from −10° C. to 100° C., for example at room temperature. Alternatively, when a flow process is used, the compound of formula (XVI) may be treated with 4-methylsulphonyl chloride in the presence of an organic base, for example N,N,N',N'-tetramethyl-1,6-hexanediamine, in dichloromethane at room temperature.

A compound of formula (XVI) may be prepared by treating a compound of formula (XVII)

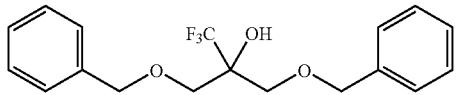
(XVII)

with a transition metal catalyst, for example 5% palladium on carbon, in the presence of a hydrogen atmosphere. The reaction may be carried out in a conventional organic solvent, for example ethanol and may be conducted using either a batch or a flow process. The reaction may be carried out at a temperature from −10° C. to 100° C., for example at room temperature for a batch process or at about 80° C. for a flow process.

A compound of formula (XVII) may be prepared by treating a compound of formula (XVIII)

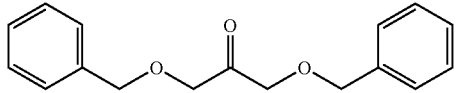
(XVIII)

with trimethyl(trifluoromethyl)silane and tetra-n-butylammonium fluoride. The reaction may be carried out in a conventional organic solvent, for example tetrahydrofuran or dichloromethane and may be conducted using either a batch or a flow process. The reaction may be carried out at a temperature from −10° C. to 100° C., for example at 0° C. rising to room temperature A compound of formula (XVIII) may be prepared by oxidation of 1,3-dibenzylglycerol. In one embodiment, the oxidation may be carried out using 3 A molecular sieves, N-methylmorpholine N-oxide and tetrapropylammonium perruthenate in dichloromethane at 0° C. to reflux, for example at room temperature. In another embodiment, the oxidation may be carried out using aqueous sodium hypochlorite, saturated sodium bicarbonate solution and 2,2,6,6-tetramethyl-1-piperidinyloxy free radical in toluene at 0° C. to 50° C., for example at room temperature. In a further embodiment, the oxidation may be carried out using sulphur trioxide-pyridine complex in the presence of base such as triethylamine in dimethylsulphoxide at 10° C. to 50° C., for example at room temperature. This oxidation may be conducted using either batch or flow processes.

Certain compounds of formulae (II), (IV), (V), (VI), (VII), (X), (XIII), (XV) and (XVII) may be new and form an aspect of the present invention.

Compounds of formula (I) may be prepared in the form of mixtures of enantiomers when mixtures of isomers are used as intermediates in the synthesis. For example, the use of a compound of formula (II) as a racemic mixture of enantiomers will lead to a mixture of enantiomers in the final product. These isomers may, if desired, be separated by conventional methods (For example by HPLC on a chiral column).

Alternatively, separation of isomers may be performed earlier in the synthesis, for example individual isomers of compounds of formula (II), (IV), (VI) or (VII) may be employed which may obviate the need to perform a separation of isomers as a final stage in the synthesis. The later process is, in theory, more efficient and is therefore preferred.

The invention will now be illustrated by way of the following non-limiting examples.

EXAMPLES

General
Abbreviations
    CDCl$_3$ Deuterochloroform
    DMF N,N-Dimethylformamide
    DMSO Dimethylsulphoxide
    EtOH Ethanol
    DCM Dichloromethane
    MeOH Methanol
    HCl Hydrochloric acid
    EtOAc Ethyl acetate
    MgSO$_4$ Magnesium sulphate
    NMR Nuclear magnetic resonance
    LCMS Liquid chromatography/mass spectrometry
    KOH Potassium hydroxide
    MeCN Acetonitrile
    BINAP (2,2'-bis(diphenylphosphino)-1,1'-binaphthyl)
    SPE Solid phase extraction
    TFA Trifluoroacetic acid
    THF Tetrahydrofuran
    RT Room temperature
    TLC Thin layer chromatography
Chromatographic Purification Chromatographic purification was performed using pre-packed silica gel cartridges. The Flashmaster II is an automated multi-user flash chromatography system, available from Argonaut Technologies Ltd, which utilises disposable, normal phase, SPE cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

Mass Directed Autopreparative HPLC:
System A:
    Agilent 1100 series LC/MSD hardware, using electrospray positive mode (ES+ve) running chemstation 32 purification software.
    Column: Zorbax Eclipse XDB-C18 prep HT (dimensions 212×100 mm, 5 μm packing), 20 ml/min solvent speed.
    Aqueous solvent=Water+0.1% TFA
    Organic solvent=MeCN+0.1% TFA
    Specific Gradients Used:
    Gradient 1 (Collects on UV/Mass Ion Trigger)

1 min 70% Water (0.1% TFA): 30% MeCN (0.1% TFA) increasing over 9 mins to 5% Water (0.1% TFA): 95% MeCN (0.1% TFA) to elute compounds.
Gradient 2 (Collects on uv Only)
1 min 70% Water (0.1% TFA): 30% MeCN (0.1% TFA) increasing over 9 mins to 5% Water (0.1% TFA): 95% MeCN (0.1% TFA) to elute compounds.
System B:
Carried out using a Micromass ZQ platform. The column was a 100 mm×20 mm Supelco LCABZ++ with stationary phase particle size of 5 μm.

| Solvents: | A: water + 0.1% formic acid |
| | B: MeCN:water 95:5 + 0.05% formic acid |
| Gradient | 50-90% B over 10 minutes |
| Flow rate | 20 ml/min |

LCMS
The LCMS system used was as follows:
Column: 3.3 cm×4.6 mm ID, 3 μm ABZ+PLUS from Supelco
Flow Rate: 3 ml/min
Injection Volume: 5 μl
Temp: RT
UV Detection Range: 215 to 330 nm

| Solvents: | A: 0.1% Formic Acid + 10 mMolar Ammonium Acetate. |
| | B: 95% Acetonitrile + 0.05% Formic Acid |

| Gradient: | | |
| --- | --- | --- |
| Time | A % | B % |
| 0.00 | 100 | 0 |
| 0.70 | 100 | 0 |
| 4.20 | 0 | 100 |
| 5.30 | 0 | 100 |
| 5.50 | 100 | 0 |

NMR
$^1$H NMR spectra were recorded in either CDCl$_3$ or DMSO-d$_6$ on either a Bruker DPX 400 or Bruker Avance DRX or Varian Unity 400 spectrometer all working at 400 MHz. The internal standard used was either tetramethylsilane or the residual protonated solvent at 7.25 ppm for CDCl$_3$ or 2.50 ppm for DMSO-d$_6$.

Intermediate 1:
1,3-Bis[(phenylmethyl)oxy]-2-propanone

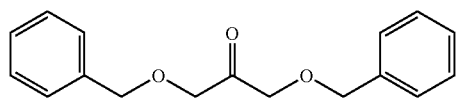

3 A Molecular sieve powder (50 g) was dried at 100° C. in a vacuum oven. The sieves and N-methylmorpholine N-oxide (35.1 g, 300 mmol) were suspended in dry dichloromethane (700 ml) before 1,3-dibenzyloxy-2-propanol (41 ml, 165 mmol) in dichloromethane (100 ml) was added to the stirred suspension. The mixture was stirred under an atmosphere of nitrogen for 90 minutes before tetrapropylammonium perruthenate (3 g, 8.53 mmol) was added. (The reaction was sufficiently exothermic to cause the dichloromethane to boil and therefore a reflux condenser was fitted.) The reaction was stirred at 21° C. for 23 hours before being filtered through celite. It was then washed with 2M hydrochloric acid (400 ml) and saturated brine (500 ml). The combined aqueous washings were filtered through celite and re-extracted with dichloromethane (500 ml) and then this was washed with saturated brine (200 ml). The organic extracts were combined, dried over magnesium sulphate and concentrated under reduced pressure to give a dark oil (43.6 g). Diethyl ether (ca. 200 ml) was added and the resultant black solid was filtered off. The filtrate was concentrated under reduced pressure to give the title compound (42 g) as a grey white solid.
$^1$H NMR (400 MHz, CHLOROFORM-d) δ ppm 7.31-7.40 (m, 10H) 4.59 (s, 4H) 4.26 (s, 4H).
LC-MS Retention Time 3.27 mins, MNH$_4^+$288.
Alternative Preparation A of Intermediate 1
A mixture of sodium hypochlorite (100 ml, 13% w/v) and saturated sodium bicarbonate (25 ml) was added in one charge to a stirred solution of 1,3-dibenzyloxy-2-propanol (10 g) and 2,2,6,6-tetramethyl-1-piperidinyloxy free radical, (TEMPO) (0.3 g) in toluene (40 ml). The biphasic mixture was stirred at 20-25° C. for 15 minutes when HPLC analysis showed reaction to be complete. The reaction mixture was stirred for a total of 25 minutes at 23° C. The reaction mixture was separated and the organic extract was washed with 5% w/v sodium thiosulfate solution (40 ml) and separated. The organic extract was washed with 1% w/v sodium chloride solution (2×25 ml). The organic extract was then concentrated in vacuo to give an oil which crystallised on standing to give 8.8 g of 1,3-dibenzyloxy-2-propanone in 88.7% yield. The NMR spectrum of the product was concordant with a reference sample.
Alternative Preparation B of Intermediate 1
A mixture of sulfur trioxide/pyridine complex (2.33 g, 4 equivalents) in DMSO (3 ml) and triethylamine (2.05 ml, 4 equivalents) was stirred to give a pale yellow solution. To this was added a solution of 1,3-dibenzyloxy-2-propanol (1 g) in DMSO (1 ml) over 2 minutes. (The reaction mixture was kept in a water bath). The temperature of the reaction mixture reached 30° C. After 10 minutes the water bath was removed and the reaction mixture was stirred at room temperature (ca 20-25° C.) for 3 hours. The reaction mixture was diluted with ethyl acetate (15 ml) and water (15 ml), stirred and the organic extract was separated. The organic extract was washed with 5% w/v sodium chloride (2×10 ml) and water (10 ml). The separated organic extract was concentrated in vacuo to give an oil which solidified to provide 0.75 g of 1,3-dibenzyloxy-2-propanone in 75.8% yield. An NMR spectrum of product was concordant with a reference sample.
Alternative Preparation C of Intermediate 1
The title compound was prepared via a 'flow' process using the following starting materials and solvents.
The title compound was prepared via a CPC Cytos Lab System made up of a 47 ml reactor block with two Jasco PU-2080Plus HPLC pumps. Reactor temperature was maintained at 60° C. via a Huber Unistat 360 unit.
Two solutions were prepared. Solution A—1,3-dibenzyloxy-2-propanol (120 g, 440 mmol) in acetonitrile (489 ml). Solution B—tetrapropylammonium perruthenate (7.72 g, 22 mmol, 5 mol %) and N-methylmorpholine N-oxide (87.5 g, 748 mmol) in acetonitrile (611 ml). Solutions A and B were pumped through the Cytos Lab system in the ratio of solution A to solution B of 1:1.25 with a total flow rate of 7.8 ml/min and residence time of 6 minutes. This gave a total reaction time of 2 hours 21 minutes. The total reacted solution was split equally into 2 batches and each was concentrated in vacuo. Diethyl ether (250 ml) was added before being washed with sodium sulphite, brine and cupric sulphate and then filtered through celite, dried and evaporated. The batches were recombined to give upon evaporation in vacuo the title compound (71.64 g).

Alternative Preparation D of Intermediate 1

A solution of 1,3-dibenzyloxy-2-propanol (500 g, 1.84 mol 1.0 eq.), TEMPO (5.5 g, 0.034 mol) in dichloromethane (1.25 L) was placed in a 10 L flange flask fitted with overhead stirrer. A solution of potassium bromide (48 g, 0.40 mol) in water (185 ml) was added and the reaction stirred and cooled to −10° C. A 14% aqueous NaOCl solution was diluted to 1M (2145 g diluted to 4050 ml). The pH of this solution was then adjusted to 9.5 by dissolving NaHCO$_3$ (80 g) immediately before use. This NaOCl solution was added over 1 hour, keeping the temperature of the reaction mixture between 10-15° C. The mixture was the stirred for 60 minutes. The orange coloured organic phase was separated and the aqueous layer was extracted with dichloromethane (5.0 L, 2.0 L). The combined organics were washed with 10% aq. HCl (10.75 L) containing potassium iodide (143 g), 10% aq. Na$_2$S$_2$O$_5$ (5.0 L) and water (5.0 L). The organics were dried over MgSO$_4$ and concentrated under reduced pressure to give the crude title compound (893 g, 90%). This compound was taken through to the next step without further purification.

Intermediate 2: 1,1,1-Trifluoro-3-[(phenylmethyl)oxy]-2-{[(phenylmethyl)oxy]methyl}-2-propanol

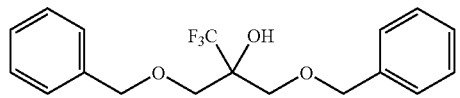

To a solution of 1,3-bis[(benzyl)oxy]-2-propanone (42 g, 155 mmol) in anhydrous tetrahydrofuran (600 ml) was added trimethyl(trifluoromethyl)silane (35 ml, 236 mmol) under nitrogen. The mixture was then cooled in an ice/ethanol bath to −3° C. before tetrabutylammonium fluoride (1M in THF, 180 ml, 180 mmol) was added dropwise (initial 10 ml of addition resulted in a slight exotherm with the temperature rising to 9° C. before being allowed to cool to 6° C. and then the addition was resumed, the temperature dropping to the range of −1° C. to +3° C.). The addition was completed after 30 minutes. The mixture was stirred for a further 4 hours during which, gas was evolved all the time and then 2M hydrochloric acid (750 ml) was added with stirring. Diethyl ether (600 ml) was added and the separated aqueous phase was reextracted with diethyl ether (1×600 ml, 1×300 ml) and the combined organic extracts were washed with saturated brine (1×300 ml), dried over sodium sulphate and concentrated under reduced pressure to give an oil (52.9 g). This oil was purified via flash chromatography (Silica, 800 g) using cyclohexane:ethyl acetate (9:1) as eluent. This gave the title compound as a yellow oil (39.5 g).

$^1$H NMR (400 MHz, CHLOROFORM-d) δ ppm 7.29-7.39 (m, 10H) 4.60 (s, 4H) 3.72 (s, 4H) 3.38 (s, 1H).

LC-MS Retention Time 3.69 mins, MNH$_4^+$358.

Alternative Preparation A of Intermediate 2

A mixture of 1,3-dibenzyloxy-2-propanone (2 g) and (trifluoromethyl)trimethylsilane (2.56 ml, 2.3 equivalents) in dichloromethane (20 ml) was stirred and cooled to 0° C. A solution of 1M tetrabutylammonium fluoride in THF (4 ml) was added dropwise over 3 minutes. Initial addition of a few drops gave an exotherm of 10° C. Throughout the addition the batch temperature was maintained below 10° C. After completing the addition the dark brown mixture was stirred at +5° C. for 5 minutes when HPLC analysis indicated the reaction to be complete. The reaction mixture was stirred for an additional 5 minutes and then washed with 1M aqueous hydrochloric acid (15 ml), saturated sodium bicarbonate (15 ml) and 1% w/v aqueous sodium chloride solution (2×15 ml). The organic extract was concentrated in vacuo to give 2.5 g of the desired product as dark oil in 99.3% yield. The NMR spectrum of the product was concordant with a reference sample.

Alternative Preparation B of Intermediate 2

Tetrabutylammonium fluoride trihydrate (TBAF 3H$_2$O) (2.9 g, 0.5 equivalent) was dissolved in THF (5 ml). This was added cautiously to a stirred and cooled (+15° C.) solution of 1,3-dibenzyloxy-2-propanone in toluene (24.65 g, equivalent to 5 g of the ketone) and (trifluoromethyl)trimethylsilane (7.5 ml). There was an exotherm and a lot of gas evolution on addition of the first 1 ml of TBAF solution. The temperature rose from 18 to 40° C. The TBAF addition was carried out over 3 minutes and then the mixture was stirred at 15-30° C. for a further 2 minutes and then cooled to +10° C. while carrying out an HPLC analysis. The reaction mixture was sequentially washed with 1M aqueous hydrochloric acid (50 ml), 1% aqueous sodium chloride solution (2×25 ml) and a mixture of 1% sodium chloride (25 ml) and saturated sodium bicarbonate (5 ml) solution. The separated organic extract was concentrated in vacuo to give 6.41 g of the desired product as dark brown oil in 101.8% yield. The NMR spectrum showed the presence of residual toluene (8.8%) and starting material (ca 3%).

Alternative Preparation C of Intermediate 2

The title compound was prepared via a 'flow' process using the following starting materials and solvents.

The title compound was prepared via a CPC Cytos Lab System made up of a 32 ml reactor block with two Jasco PU-2080Plus HPLC pumps. Reactor temperature was maintained at 22° C. via a Huber Unistat 360 unit. The reactor outlet was fitted with a 100 psi backflow regulator.

Two solutions were prepared. Solution A—1,3-dibenzyloxy-2-propanone (71.64 g, 265 mmol) and trimethyl(trifluoromethyl)silane (86.7 g, 96 ml, 609.5 mmol) in tetrahydrofuran (99 ml). Solution B—tetrabutylammonium fluoride (0.5M in THF, 265 ml, 132.5 mmol). Solutions A and B were pumped through the Cytos Lab System with a flow rate of 6.4 ml/min and a 5 minute residence time giving a total reaction time of 82 minutes. The reaction mixture was quenched with 2M hydrochloric acid (560 ml) and then divided into 2 equal batches (2×280 ml). Diethyl ether (100 ml) was added to each batch, extracted and then washed with brine (2×100 ml), dried (MgSO$_4$) and evaporated to give a residue (82.99 g). Part of the residue was taken up in dichloromethane and applied to SPE silica cartridges. Using 10% hexane in dichloromethane as eluent and concentration of the relevant 15 ml fractions, the title compound was obtained. The bulk of the crude sample was purified on the Combiflash Companion XL. 8 g of material was run on a 120 g column with a solvent gradient of 10%-70% dichloromethane in hexane as eluent. Any mixed fractions from each run were combined and repurified in an identical manner. All pure fractions were combined and evaporated to give the title compound (68.68 g).

Alternative Preparation D of Intermediate 2

A solution of 1,3-dibenzyloxy-2-propanone (310 g, 1.15 mol, 1.0 eq.) was placed in a 10 L flange flask, equipped with magnetic stirrer, condenser under argon, followed by THF (3.5 L). This was stirred at 15° C. Trimethyl(trifluoromethyl)silane (TMS-CF$_3$) (Matrix, 231 g, 1.62 mol, 1.41 eq.) was added dropwise over 1 hour. The solution was then cooled to 0° C. using an ice-water bath and tetrabutylammonium fluoride (TBAF) (337 g, 1.29 L, 1M in THF, 1.29 mol, 1.12 eq.) was added dropwise keeping the temperature in the range 0-8° C. (initial sharp delayed exotherms). After the addition was complete, the temperature was raised cautiously to 20° C. and the reaction stirred at 27° C. overnight (oil bath). (TLC Rf starting material=0.3, product=0.4, 80:20 petroleum ether/ ethyl acetate showed reaction was essentially complete). Reaction mixture was then cooled to 15° C. using an ice-water bath, then quenched by slow addition of 1M HCl (10.5 L) (transfer to a 20 L separator after 1.0 L added). The mixture was extracted with diethyl ether (3×5.0 L). The combined organics were washed with water (2.5 L) and brine (2.5 L). The organics were dried over MgSO₄ and concentrated under reduced pressure to yield a brown oil (388 g with THF).

Intermediate 3:
2-(Trifluoromethyl)-1,2,3-propanetriol

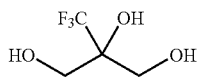

A solution of 1,1,1-trifluoro-3-[(benzyl)oxy)]-2-{[(benzyl)oxy]methyl}-2-propanol (98.9 g, 290.9 mmol) in ethanol (1750 ml) was added to 5% palladium on carbon (9.73 g, wet, Degussa, E101 No/W) under nitrogen. The mixture was then stirred under an atmosphere of hydrogen using a Wright valve in a 5 liter hydrogenation vessel. After approximately 3 hours most of the theoretical volume of hydrogen had been taken up. After stirring under hydrogen overnight (approximately a further 1 liter of hydrogen had been taken up overnight), the catalyst was filtered off through a pad of celite and the pad washed with ethanol. The filtrate and washings were then concentrated under reduced pressure and the residue azeotroped (×2) with dichloromethane whereupon the residue became solid. This material was left on the vacuum pump to give the title compound (48.56 g) as an off white solid.

$^1$H NMR (400 MHz, DMSO-d₆) δ ppm 5.65 (s, 1H) 4.89 (t, 2H) 3.54 (d, J=5.8 Hz, 4H).

LC-MS Retention Time 0.42 mins, ES⁻159.

Alternative Preparation A of Intermediate 3

The title compound was prepared employing the Thales H-Cube hydrogenator and milligat pump in full hydrogen mode. A solution of 1,1,1-trifluoro-3-[(phenylmethyl)oxy]-2-{[(phenylmethyl)oxy]methyl}-2-propanol (58 g) in ethanol (580 ml) was prepared. The flow rate was 1.3 ml/min, the temperature was set to 80° C. and the cartridge employed was a 10% Pd/C Cat Cart 70 which was replaced every 2 hours. Any fractions which still contained starting material and the mono benzyl intermediate were reprocessed. All pure fractions were combined and evaporated to give the title compound (26.48 g).

Alternative Preparation B of Intermediate 3

1,1,1-Trifluoro-3-[(benzyl)oxy]-2-{[(benzyl)oxy]methyl}-2-propanol (1.3 kg, 3.82 mol, 1.0 eq.) was placed in a 10 L flange flask equipped with a overhead stirrer, followed by ethanol (4.5 L). 10% palladium on carbon (27 g) was added under Argon atmosphere. The reaction was then subjected to hydrogenolysis at atmospheric pressure (6 balloons) and stirred overnight at 50° C. (the balloons were topped up repeatably during the day). $^1$H NMR showed completion of reaction had been reached after 1 week, required additional 10% palladium on carbon (4 g). The reaction mixture was filtered through a pad of celite and washed with ethanol (2.5 L). The filtrate was concentrated under reduced pressure to give an oil. This was placed under high vacuum overnight to obtain a solid material. Toluene (1.5 L) was added and the mixture heated until the solid dissolved (~60° C.), 2 layers were observed. The mixture was stirred using a magnetic stirrer and cooled using an ice-water bath, where a solid precipitated. The solid was broken up and stirred for a further 30 minutes, then isolated by filtration. The solid was washed with toluene (250 ml) and petroleum ether (250 ml). The solid was dried under high vacuum overnight to yield desired product (465 g).

Intermediate 4: 3,3,3-Trifluoro-2-hydroxy-2-({[(4-methylphenyl)sulfonyl]oxy}methyl)propyl 4-methylbenzenesulfonate

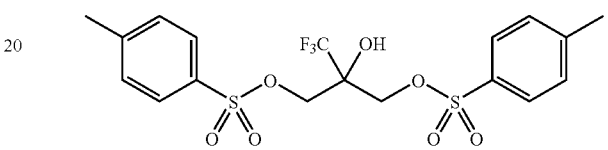

To a stirred solution of 2-(trifluoromethyl)-1,2,3-propanetriol (18.9 g, 118 mmol) in pyridine (200 ml) which had been cooled in an ice bath was added p-toluenesulphonyl chloride (67 g, 351 mmol) to give an orange solution. The ice bath was removed after 45 minutes and stirring was continued for 21 hours during which time a solid formed. Most of the pyridine was removed under reduced pressure and the residue was partitioned between ethyl acetate (500 ml) and water (300 ml). The separated aqueous phase was further extracted with ethyl acetate (1×250 ml) and the combined organic extracts were washed with 2M hydrochloric acid (1×200 ml), water (1×200 ml), saturated sodium bicarbonate (1×200 ml), water (1×200 ml) and saturated brine (1×200 ml) before being dried over sodium sulphate and concentrated under reduced pressure to give an oil (72.8 g). This oil was purified on a Flash silica column (800 g) eluting with cyclohexane:ethyl acetate (5:1) to give the title product (49 g, 95%) as an oil which crystallised on standing.

$^1$H NMR (400 MHz, CHLOROFORM-d) δ ppm 7.78 (d, J=8.3 Hz, 4H) 7.38 (d, J=8.3 Hz, 4H) 4.18 (s, 4H) 3.66 (s, 1H) 2.48 (s, 6H).

LC-MS Retention Time, 3.62 mins, MNH₄⁺486, ES⁻467.

Alternative Preparation A of Intermediate 4

The title compound was prepared via a 'flow' process using the following starting materials and solvents.

Two solutions were prepared. Solution A—2-(trifluoromethyl)-1,2,3-propanetriol (4.5 g, 27.8 mmol), N,N,N',N'-tetramethyl-1,6-hexanediamine (30 ml, 139 mmol), dichloromethane (550 ml). Solution B—p-toluenesulphonyl chloride (21.4 g, 111 mmol), dichloromethane (550 ml).

Solutions A and B were pumped through a CPC Cytos reactor (reactor volume 47 ml) at a flow rate each of 2.35 ml/min. It was noted that the pressure for the pump containing solution B was fluctuating. After 110 minutes, the reaction was abandoned as it was evident that the pumps were not operating 1:1. The collected material was extracted with dichloromethane (×3) before being washed with brine, dried (MgSO₄), filtered and concentrated to give a residue which was discarded. The pump was replaced and the remainder of the reagents were reacted. The collected material was extracted with dichloromethane (×3) before being washed with brine, dried (MgSO₄), filtered and concentrated to give a residue. It was adsorbed onto silica and eluted over a silica column (12 g) with dichloromethane:hexane (1:1). Four fractions were eluted and fraction 4 gave the title compound (2.31 g).

Alternative Preparation B of Intermediate 4

2-(Trifluoromethyl)-1,2,3-propanetriol (300 g, 1.86 mol, 1.0 eq.) was dissolved in pyridine (2.0 L) in a 10 L flange flask fitted with an overhead stirrer, thermoprobe under argon. This was cooled to 0° C. with a solid $CO_2$-acetone bath. Tosyl chloride (809 g, 4.1 mol, 2.2 eq) was added portionwise, maintaining temperature <10° C. On completion of addition, the cold bath was removed and reaction mixture allowed to stir at room temperature overnight. The reaction mixture was filtered and concentrated under reduced pressure. The resulting brown oil was partitioned between EtOAc (4.0 L) and 2M HCl (4.0 L), stirred for 5 minutes and separated. The aqueous layer was further extracted with EtOAc (2×2.5 L). The combined organics were washed with saturated $NaHCO_3$ (3.5 L, 5 mins stir period), brine (2.5 L) and dried over $MgSO_4$. This was concentrated under reduced pressure to give a thick brown oil. The crude material was taken to the next step without further purification (950 g, overweight, assume 100%).

Intermediate 5:
[2-(Trifluoromethyl)-2-oxiranyl]methyl 4-methylbenzenesulfonate

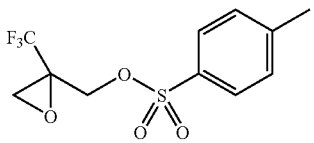

A solution of the 3,3,3-trifluoro-2-hydroxy-2-({[(4-methylphenyl) sulfonyl]oxy}methyl)propyl 4-methylbenzenesulfonate (186.5 g, 398.5 mmol) in dichloromethane (2500 ml) was stirred under nitrogen whilst polymer supported carbonate resin (ex Fluke, ca. 3.5 mmoles carbonate/g resin) (232 g) was added. The mixture was stirred at room temperature overnight. The resin was filtered off and the resin was washed with dichloromethane. The combined filtrate and washings were concentrated under reduced pressure to give the title compound (116.2 g) as a brown oil.

$^1$H NMR (400 MHz, CHLOROFORM-d) δ ppm 7.80 (d, J=8.3 Hz, 2H) 7.38 (d, J=8.0 Hz, 2H) 4.41 (d, J=11.9 Hz, 1H) 4.29 (d, J=11.9 Hz, 1H) 3.14 (d, J=4.8 Hz, 1H) 3.01 (dd, J=4.5, 1.5 Hz, 1H) 2.47 (s, 3H).

LC-MS Retention Time 3.2 mins, $MNH_4^+$ 314.

Alternative Preparation A of Intermediate 5

3,3,3-Trifluoro-2-hydroxy-2-({[(4-methylphenyl)sulfonyl]oxy}methyl)propyl 4-methylbenzenesulfonate (14.29 g, 29 mmol) in dichloromethane (75 ml) was pumped through a cartridge containing PS-carbonate resin (not pre-swelled) (3 mmol/g, 25 g, 75 mmol) at 675 microliters/min. The temperature was set to approx. 50° C. by wrapping a Whatman thin film heater around the cartridge. The pressure was regulated at 40 psi. After all the reagent had been aspirated, the column was washed through with dichloromethane—at this point the column started to leak slightly and the back pressure regulator had to be removed to reduce the pressure. The collected solution was concentrated in vacuo to afford the title compound (7.25 g).

Alternative Preparation B of Intermediate 5

Bis tosylate, 3,3,3-trifluoro-2-hydroxy-2-({[(4-methylphenyl) sulfonyl]oxy}methyl)propyl 4-methylbenzenesulfonate (1.047 kg, 2.24 mol, 1.0 eq.) was dissolved in dichloromethane (9.0 L) in a 20 L flange flask, fitted with overhead stirrer under argon. Potassium carbonate (1.24 kg, 8.95 mol, 4.0 eq.) was added portionwise over 8 hours and stirred overnight at room temperature. $^1$H NMR showed ~41% completion of reaction. Additional potassium carbonate (600 g, 2.0 eq.) was added over 8 hours and stirred overnight. $^1$H NMR showed 89% completion of reaction. Additional potassium carbonate (300 g, 1.0 eq.) was added over 8 hours and stirred overnight. $^1$H NMR showed completion of reaction reached. The reaction mixture was filtered on two glass sinters with a pad of celite and washed with dichloromethane. The filtrate was washed with $NaHCO_3$ (3.5 L), brine (2.5 L) and dried over $MgSO_4$. The filtrate was then concentrated under reduced pressure to give a dark red oil. The crude product was purified by suction chromatography (~13 cm silica on 4 L sinter, collected ~1.5 L fractions, starting with 95:5 petroleum ether/EtOAc as eluent until all the tosyl chloride was removed, the polarity of the eluent was then increased slowly to 90:10, 80:20 and 70:30. TLC was run with 70:30 Petroleum ether/EtOAc giving Rf tosyl chloride=0.55, Product=0.5, impurity=0.3. Some mixed fractions were obtained, they were re-columned using same conditions as above. This gave clean product (417 g, 63%) as an orange oil, which solidified with high vacuum overnight.

Intermediate 6: 4-Nitro-1-phenyl-1H-indazole

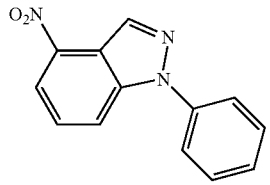

2,6-Dinitrobenzaldehyde (2.8 g, 14 mmol) (which may be prepared according to the method of Lulinski and Serwatowski, *Journal of Organic Chemistry*, 68, (2003), 5384) and phenylhydrazine (1.7 g, 17 mmol) were dissolved in a mixture of EtOH (20 ml) and acetic acid (2 ml) resulting in a red solution. After stirring for 2 hours the solution was concentrated to a red solid which was dissolved in EtOH (250 ml) and a solution of potassium hydroxide (2 g) in water (30 ml) was added. After stirring for 2 hours the solution was concentrated to a black solid which was dissolved in EtOAc (1 L), washed with 1M HCl (3×500 ml), saturated sodium bicarbonate and brine (250 ml). The organic solution was dried and concentrated to a brown solid which was applied to a silica column. Elution with a 10%-50% gradient of EtOAc in hexane isolated the title compound as a yellow solid.

$^1$H-NMR: ($CDCl_3$, 400 MHz) δ 8.85 (s, 1H), 8.22 (d, 1H), 8.06 (d, 1H), 7.70 (m, 2H), 7.6 (m, 3H), 7.46 (m, 1H)

Intermediate 7: 1-Phenyl-1H-indazol-4-amine

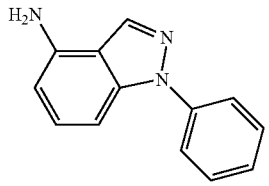

Method A

6-Nitro-1-phenyl-1H-indazole was dissolved in EtOAc (200 ml) then 10% Pd/C (500 mg) was added and the mixture was stirred under a hydrogen atmosphere for 2 hours. Filtration through celite and concentration of the filtrate gave a yellow oil which was dissolved in diethyl ether (100 ml). A solution of 4M HCl in dioxan (10 ml) was added slowly resulting in a yellow precipitate which was filtered off to give the title compound as the hydrochloride salt as a yellow solid (2.5 g).

$^1$H-NMR: (DMSO-d$_6$, 400 MHz) δ 8.4 (s, 1H), 7.71 (m, 2H), 7.55 (t, 2H), 7.35 (t, 1H), 7.22 (t, 1H), 7.14 (m, 1H), 6.53 (d, 1H), 5.40 (broad s)

Method B

A suspension of 1H-indazol-4-amine (1 g, 7.52 mmol), copper (I) iodide (71.3 mg, 3.75 mmol) and potassium phosphate (3.3 g, 15.77 mmol) in toluene (30 ml) was degassed and then iodobenzene (1 ml, 9.02 mmol) and trans-N,N'-dimethyl-1,2-cyclohexanediamine (213.2 mg, 1.5 mmol) were added and the mixture stirred at 110° C. overnight. More iodobenzene (0.5 ml, 4.51 mmol), potassium phosphate (1.7 g, 8 mmol), copper (I) iodide (35.1 mg, 1.85 mmol) and trans-N,N'-dimethyl-1,2-cyclohexanediamine (106.1 mg, 0.75 mmol) were then added and stirring continued at 110° C. over the weekend. The mixture was cooled, diluted with ethyl acetate (20 ml), filtered through celite, washing through with ethyl acetate and the combined filtrate and washings evaporated. The residue was purified by silica gel chromatography using the Flashmaster II (100 g cartridge) eluting with a 0 to 50% dichloromethane:ethyl acetate gradient over 60 minutes to give the title compound (519 mg).

LCMS: $t_{RET}$=3.05 min; MH$^+$=210

Intermediate 8: 1-(4-Fluorophenyl)-1H-indazol-4-amine

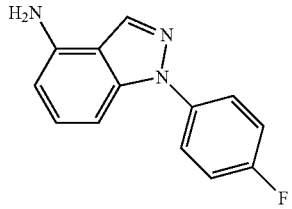

A mixture of 1H-indazol-4-amine (750 mg, 5.64 mmol), copper (I) iodide (247 mg, 1.3 mmol), potassium carbonate (1.56 g, 11.28 mmol), trans-N,N'-dimethyl-1,2-cyclohexanediamine (0.321 g, 2.26 mmol) and 4-fluoro-1-iodobenzene (0.78 ml, 6.77 mmol) in dry DMF (2 ml) was heated in a microwave reactor at 140° C. for 20 minutes (potassium carbonate was placed in the tube first and care was taken to avoid any particles of potassium carbonate being left on the side of the tube above the level of the liquid (in order to avoid any superheating). Three identical reactions plus two using 500 mg input of 1H-indazol-4-amine were then combined and partitioned between water and dichloromethane. The organic layer was evaporated and the residue purified by silica gel chromatography using the Flashmaster II (2×100 g cartridges) eluting with a 0 to 50% dichloromethane:ethyl acetate gradient over 60 minutes to give the title compound (4.73 g).

LCMS: $t_{RET}$=3.19 min; MH$^+$=228

Intermediate 9: 6-Methyl-1-phenyl-1H-indazol-4-amine

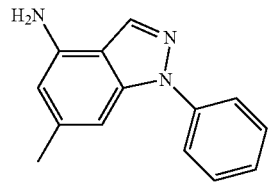

6-Methyl-1H-indazol-4-amine (75 mg, 0.51 mmol) and iodobenzene (104 mg, 0.51 mmol) were dissolved in DMF (0.55 ml) in a microwave tube. Copper (I) iodide (19 mg, 0.1 mmol), trans-N,N'-dimethyl-1,2-cyclohexanediamine (28.5 mg, 0.2 mmol) and potassium carbonate (140.9 mg, 1.02 mmol) were added and the mixture heated by microwave (250 W) at 100° C. for 20 minutes. The mixture was filtered through a cartridge, washing with DCM (5 ml) and the filtrate was evaporated to dryness and purified by mass-directed autopreparation (system B). The appropriate fractions were combined, extracted with DCM, washed with aqueous sodium bicarbonate, dried through a hydrophobic frit and evaporated to give the title compound (34.9 mg).

LCMS: $t_{RET}$=3.26 min; MH$^+$=224

Intermediate 10: 1-(4-Fluorophenyl)-6-methyl-1H-indazol-4-amine

A mixture of 4-bromo-1-(4-fluorophenyl)-6-methyl-1H-indazole (8.584 g, 28.114 mmole), tris(dibenzylideneacetone)dipalladium(0) (128.5 mg, 0.14 mmol), racemic BINAP (262.6 mg, 0.42 mmol), benzophenone imine (8.13 g, 44.86 mmol) and sodium tert-butoxide (3.78 g, 39.33 mmol) in toluene (75 ml) was heated at 80° C. for 27 hours. The cooled mixture was filtered through a short silica gel column washing through with chloroform and ethyl acetate. The eluent was evaporated and the residue then purified by silica gel chromatography eluting firstly with chloroform and finally with chloroform containing some ethyl acetate to give the intermediate imine (8.334 g). This material was dissolved in THF (80 ml) and 2M HCl (12 ml) was added. After 1 hour dilute HCl was added and the mixture was evaporated to leave a white solid which was triturated with cyclohexane and the solid collected. This material was suspended in water and sufficient aqueous sodium hydroxide was added to make the mixture alkaline and the product was extracted into chloroform. Evaporation of the chloroform extract gave the title compound (4.77 g)

LCMS: $t_{RET}$=3.17 min; MH$^+$=242

Intermediate 11: 1-Phenyl-N-{[2-(trifluoromethyl)-2-oxiranyl]methyl}-1H-indazol-4-amine

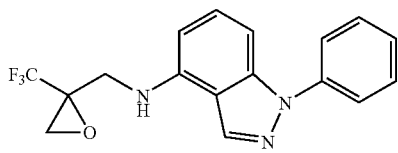

Bismuth chloride (623 mg, 1.98 mmol) was added to a suspension of [2-(trifluoromethyl)-2-oxiranyl]methyl 4-methylbenzenesulfonate (5.85 g, 19.76 mmol) and 1-phenyl-1H-indazol-4-amine (4.13 g, 19.76 mmol) in dry dichloromethane (8 ml) and the mixture stirred at room temperature over the weekend. The resulting thick suspension was diluted with dichloromethane and stirred overnight. The mixture was then diluted with chloroform (200 ml) and sodium sulphate (30 g) and polymer supported carbonate resin (Fluka, ca. 3.5 mmoles carbonate/g resin, 11 g) were added and the mixture stirred overnight. LCMS showed no evidence for cyclisation to the target epoxide. Dry tetrahydrofuran (50 ml) and N,N-diisopropylethylamine (0.85 ml, 4.88 mmol) were then added and the mixture stirred overnight when LCMS indicated complete reaction. The mixture was filtered and the filtrate was washed with water. The aqueous phase was back-extracted with dichloromethane and the combined organic phases were dried and evaporated to give crude product which was purified by silica gel chromatography using the Flashmaster II (2×100 g cartridges) eluting with a 0 to 50% dichloromethane:ethyl acetate gradient over 40 minutes to give the title compound (3.74 g).

LCMS: $t_{RET}$=3.66 min; MH$^+$=334

Intermediate 12: 1-(4-Fluorophenyl)-N-{[2-(trifluoromethyl)-2-oxiranyl]methyl}-1H-indazol-4-amine

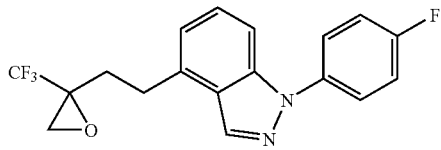

[2-(trifluoromethyl)-2-oxiranyl]methyl 4-methylbenzenesulfonate (6.14 g, 20.75 mmol) and 1-(4-fluorophenyl)-1H-indazol-4-amine (4.73 g, 20.75 mmol) in dry dichloromethane (5 ml) were stirred for 5 min. Bismuth chloride (654 mg, 2.07 mmol) was added and the mixture stirred at room temperature over the weekend. More bismuth chloride (0.33 g, 1.05 mmol) was then added and the mixture stirred overnight. The reaction was finally stirred overnight under nitrogen (to reduce the volume of DMF). There was no further progress on leaving for a further night. The reaction mixture was then diluted with chloroform (200 ml) and tetrahydrofuran (50 ml). N,N-Diisopropylethylamine (0.54 ml, 3.11 mmol) was added followed by polymer supported carbonate resin (Fluka, ca. 3.5 mmoles carbonate/g resin, 11.91 g) and the mixture stirred overnight. More THF (30 ml) was then added followed after 2 hours by some 4 A molecular sieves. After a further 3 hours LCMS indicated the reaction to be complete and the mixture was filtered. The filtrate was washed with water, the aqueous phase was back-extracted with dichloromethane and the combined organic phases were dried and evaporated to give crude product which was purified by silica gel chromatography using the Flashmaster II (2×100 g cartridges) eluting with a 0 to 50% dichloromethane:ethyl acetate gradient to give the title compound (4.31 g).

LCMS: $t_{RET}$=3.68 min; MH$^+$=352

Intermediate 13: 6-Methyl-1-phenyl-N-{[2-(trifluoromethyl)-2-oxiranyl]methyl}-1H-indazol-4-amine

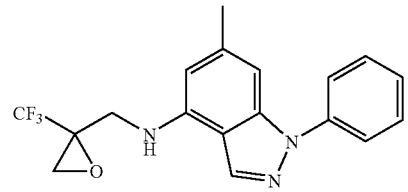

Bismuth chloride (347 mg, 1.1 mmol) was added to a mixture of [2-(trifluoromethyl)-2-oxiranyl]methyl 4-methylbenzenesulfonate (3.41 g, 11.5 mmol) and 6-methyl-1-phenyl-1H-indazol-4-amine (2.45 g, 1.1 mmol) in dry dichloromethane (4.5 ml) and the mixture stirred at room temperature under nitrogen over the weekend. More bismuth chloride (173 mg, 0.55 mmol) and dichloromethane (0.5 ml) were then added and the mixture stirred overnight and then diluted with chloroform (50 ml) and dry tetrahydrofuran (25 ml). N,N-Diisopropylethylamine (0.38 ml, 2.2 mmol) was added followed by polymer supported carbonate resin (Fluka, ca. 3.5 mmoles carbonate/g resin, 9.4 g) and 4 A molecular sieves. After 6 hours LCMS indicated the reaction to be complete and the mixture was filtered. The filtrate was washed with water, the aqueous phase was back-extracted with dichloromethane and the combined organic phases were dried and evaporated to give crude product which was purified by silica gel chromatography using the Flashmaster II (100 g cartridge) eluting with a 0 to 100% cyclohexane:ethyl acetate gradient. Product containing fractions were combined with similar fractions from a parallel reaction (1.28 g input of Intermediate 9) to give the title compound (2.67 g).

LCMS: $t_{RET}$=3.62 min; MH$^+$=348

Intermediate 14: 1-(4-Fluorophenyl)-6-methyl-N-{[2-(trifluoromethyl)-2-oxiranyl]methyl}-1H-indazol-4-amine

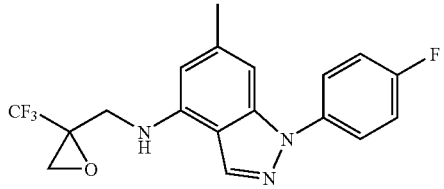

Bismuth chloride (630 mg, 2 mmol) was added to a solution of [2-(trifluoromethyl)-2-oxiranyl]methyl 4-methylbenzenesulfonate (5.915 g, 19.98 mmol) and 1-(4-fluorophenyl)-6-methyl-1H-indazol-4-amine (4.742 g, 19.67 mmol) in dry dichloromethane (14 ml) and the mixture stirred at room temperature under nitrogen for 3 days. More bismuth chloride (620 mg, 1.97 mmol), 2-(trifluoromethyl)-2-oxiranyl]methyl 4-methylbenzenesulfonate (300 mg, 1.01 mmol) and a small amount of dichloromethane were then added and the mixture stirred over the weekend. The mixture was then diluted with chloroform and tetrahydrofuran and then washed with aqueous sodium bicarbonate. The aqueous layer was back-extracted with chloroform and the combined organic phases were dried over anhydrous sodium sulphate and evaporated to leave a brown oil (ca. 12 g). This crude intermediate was dissolved in chloroform (250 ml) and polymer supported carbonate resin (Fluka, ca. 3.5 mmoles carbonate/g resin, 16.88 g) was added and the mixture stirred overnight. The resin was removed by filtration, washing with chloroform and the combined filtrate and washings were evaporated and the residue (9.1 g) purified by silica gel chromatography using firstly dichloromethane and then dichloromethane/ethyl acetate as eluent. Product containing fractions were combined and evaporated to give the title compound (3 g).

LCMS: $t_{RET}$=3.6 min; MH$^+$=366

Intermediate 15: 3-(Ethylamino)-1,1,1-trifluoro-2-{[(1-phenyl-1H-indazol-4-yl)amino]methyl}-2-propanol

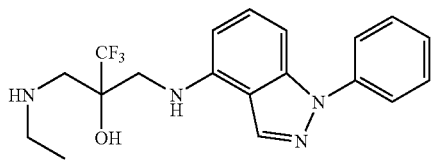

To a solution of 1-phenyl-N-{[2-(trifluoromethyl)-2-oxiranyl]methyl}-1H-indazol-4-amine (1.235 g, 3.7 mmol) in anhydrous tetrahydrofuran (5 ml) was added ethylamine (2M in tetrahydrofuran) (10 ml, 20 mmol). The reaction was stirred at room temperature for approximately 72 hours and then evaporated in vacuo to give the title compound.

LCMS: $t_{RET}$=2.47 min; MH$^+$=379

Intermediate 16: 3-(Ethylamino)-1,1,1-trifluoro-2-({[1-(4-fluorophenyl)-1H-indazol-4-yl]amino}methyl)-2-propanol

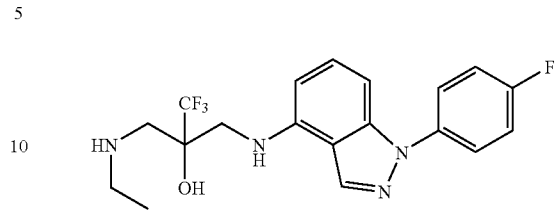

Prepared similarly to Intermediate 15 from ethylamine (2M in tetrahydrofuran) and 1-(4-fluorophenyl)-N-{[2-(trifluoromethyl)-2-oxiranyl]methyl}-indazol-4-amine.

LCMS: $t_{RET}$=2.53 min; MH$^+$=397

Intermediate 17: 1,1,1-Trifluoro-3-{[1-(4-fluorophenyl)-1H-indazol-4-yl]amino}-2-[(propylamino)methyl]-2-propanol

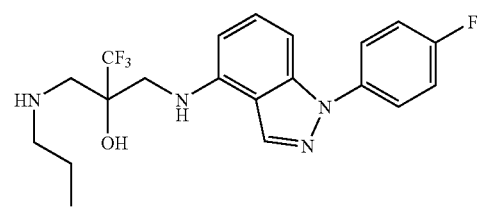

Prepared similarly to Intermediate 15 from n-propylamine and 1-(4-fluorophenyl)-N-{[2-(trifluoromethyl)-2-oxiranyl]methyl}-1H-indazol-4-amine.

LCMS: $t_{RET}$=2.81 min; MH$^+$=411

Intermediate 18: 3-(Ethylamino)-1,1,1-trifluoro-2-{[(6-methyl-1-phenyl-1H-indazol-4-yl)amino]methyl}-2-propanol

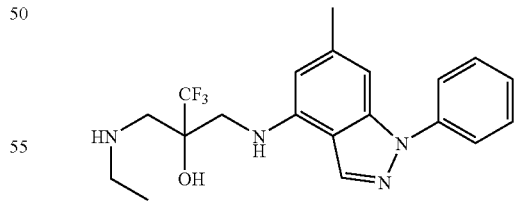

To a solution of 6-methyl-1-phenyl-N-{[2-(trifluoromethyl)-2-oxiranyl]methyl}-1H-indazol-4-amine (1.1 g, 3.17 mmol) in anhydrous tetrahydrofuran (5 ml) was added ethylamine (2M in tetrahydrofuran) (10 ml, 20 mmol). The reaction was stirred at room temperature for 6 hours and then evaporated in vacuo to give the title compound (1.28 g).

LCMS: $t_{RET}$=2.76 min; MH$^+$=393

Intermediate 19: 1,1,1-Trifluoro-3-[(6-methyl-1-phenyl-1H-indazol-4-yl)amino]-2-[(propylamino)methyl]-2-propanol

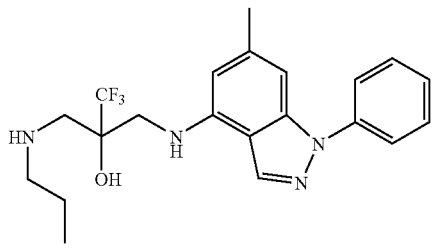

Prepared similarly to Intermediate 18 from n-propylamine and 6-methyl-1-phenyl-N-{[2-(trifluoromethyl)-2-oxiranyl]methyl}-1H-indazol-4-amine.

LCMS: $t_{RET}$=2.80 min; MH$^+$=407

Intermediate 20: 3-(Ethylamino)-1,1,1-trifluoro-2-({[1-(4-fluorophenyl)-6-methyl-1H-indazol-4-yl]amino}methyl)-2-propanol

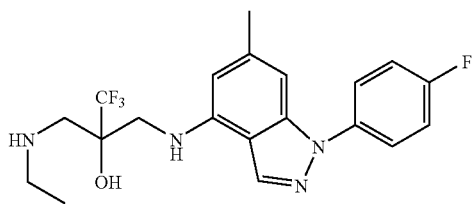

A solution of 1-(4-fluorophenyl)-6-methyl-N-{[2-(trifluoromethyl)-2-oxiranyl]methyl}-1H-indazol-4-amine (1.52 g, 4.16 mmol) in dichloromethane (30 ml) was added to ethylamine (2M in tetrahydrofuran) (70 ml, 140 mmol). The reaction was stirred at room temperature overnight and then evaporated in vacuo. The crude product was purified on a 70 g silica Bond Elut cartridge using a 0-100% ethyl acetate in dichloromethane gradient over 60 mins to give the title compound (1.463 g).

LCMS: $t_{RET}$=2.25 min; MH$^+$=411

Intermediate 21: 1,1,1-Trifluoro-3-{[1-(4-fluorophenyl)-6-methyl-1H-indazol-4-yl]amino}-2-[(propylamino)methyl]-2-propanol

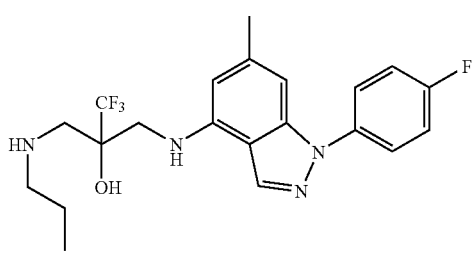

To a solution of 1-(4-fluorophenyl)-6-methyl-N-{[2-(trifluoromethyl)-2-oxiranyl]methyl}-1H-indazol-4-amine (1.4 g, 3.84 mmol) in dichloromethane (50 ml) was added n-propylamine (20 ml, 243 mmol). The reaction was stirred at room temperature overnight and then evaporated in vacuo. The crude product was purified on a 70 g silica Bond Elut cartridge using a 0-50% ethyl acetate in dichloromethane gradient over 60 minutes to give the title compound (0.4 g).

LCMS: $t_{RET}$=2.60 min; MH$^+$=425

Intermediate 22: 1,1,1-Trifluoro-3-[(1-phenyl-1H-indazol-4-yl)amino]-2-[(propylamino)methyl]-2-propanol

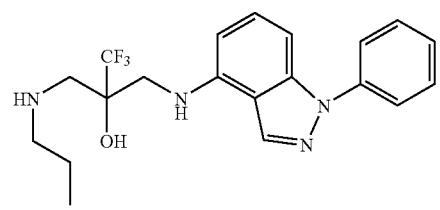

Prepared similarly to Intermediate 15 from n-propylamine and 1-phenyl-N-{[2-(trifluoromethyl)-2-oxiranyl]methyl}-1H-indazol-4-amine.

LCMS: $t_{RET}$=2.55 min; MH$^+$=393

Intermediate 23: 2,6-Dibromo-4-methylbenzaldehyde (4-fluorophenyl)hydrazone

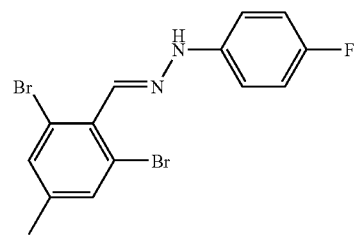

2,6-Dibromo-4-methylbenzaldehyde (600 g, 2.16 mmol) (which may be prepared according to the method of Lulinski and Serwatowski, *Journal of Organic Chemistry*, 68, (2003), 5384), (4-fluorophenyl)hydrazine hydrochloride (351 mg, 2.16 mmol) and sodium acetate (180 mg, 2.19 mmol) were heated in methanol (15 ml) under reflux for 2 hours in a nitrogen atmosphere. The methanol was evaporated and the residue partitioned between dichloromethane (30 ml) and aqueous brine (30 ml). The organic phase was separated, combined with additional dichloromethane extracts (2×15 ml), washed with aqueous sodium bicarbonate (2×15 ml), passed through a hydrophobic frit and evaporated to give the title compound (809 mg).

LCMS: $t_{RET}$=4.23 min; MH$^+$=387

Intermediate 24:
4-Bromo-1-(4-fluorophenyl)-6-methyl-1H-indazole

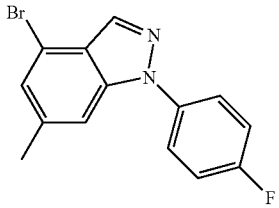

6-Dibromo-4-methylbenzaldehyde (4-fluorophenyl)hydrazone (811 mg, 2.1 mmol), tripotassium phosphate (1.1 g, 5.25 mmol), tris(dibenzylideneacetone)dipalladium(0) (77 mg, 0.084 mmol) and racemic BINAP (52 mg, 0.084 mmol) were dissolved in toluene (27.5 ml) and heated under reflux for 16 hours in a nitrogen atmosphere. The mixture was then cooled and evaporated under reduced pressure and the residue purified by silica gel chromatography using the Flashmaster II (100 g cartridge) eluting with a 100:0 to 0:100 cyclohexane:dichloromethane gradient over 40 minutes to give the title compound (243 mg).

LCMS: $t_{RET}$=3.90 min; MH$^+$=305/307

Example 1

N-Ethyl-N-(3,3,3-trifluoro-2-hydroxy-2-{[(1-phenyl-1H-indazol-4-yl)amino]methyl}propyl)benzamide

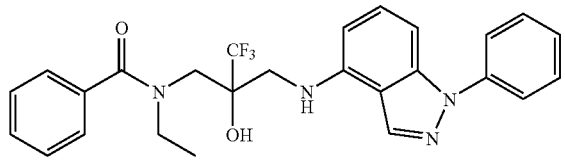

To benzoic acid (11 mg, 0.09 mmol) was added a solution of O-(7-azabenzotriazol-1-yl)-N,N,N',N'-tetramethyluronium hexafluorophosphate (34 mg, 0.09 mmol) in DMF (0.2 ml) followed by N,N-diisopropylethylamine (32 µL, 0.182 mmol). The mixture was shaken for 1 minute and then a solution of 3-(ethylamino)-1,1,1-trifluoro-2-{[(1-phenyl-1H-indazol-4-yl)amino]methyl}-2-propanol (26 mg, 0.07 mmol) in DMF (0.2 ml) was added. The mixture was again shaken for 1 minute and then left to stand at room temperature for 18 hours. The crude reaction was diluted with dimethyl sulfoxide (0.1 ml) and purified by mass-directed autopreparation (system A) to give the title compound (20.7 mg).

LCMS: $t_{RET}$=3.64 min; MH$^+$=483

Example 2

N-Ethyl-2-methyl-N-(3,3,3-trifluoro-2-hydroxy-2-{[(1-phenyl-1H-indazol-4-yl)amino]methyl}propyl)benzamide

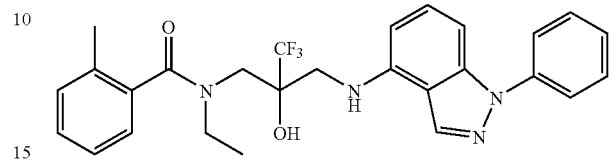

Prepared similarly to Example 1 from 2-methylbenzoic acid and 3-(ethylamino)-1,1,1-trifluoro-2-{[(1-phenyl-1H-indazol-4-yl)amino]methyl}-2-propanol.

LCMS: $t_{RET}$=3.73 min; MH$^+$=497

Example 3

N-Ethyl-2-fluoro-N-(3,3,3-trifluoro-2-hydroxy-2-{[(1-phenyl-1H-indazol-4-yl)amino]methyl}propyl)benzamide

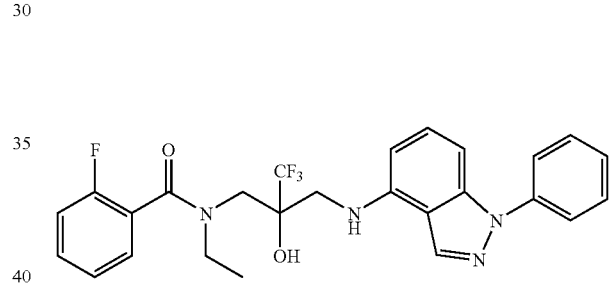

Prepared similarly to Example 1 from 2-fluorobenzoic acid and 3-(ethylamino)-1,1,1-trifluoro-2-{[(1-phenyl-1H-indazol-4-yl)amino]methyl}-2-propanol.

LCMS: $t_{RET}$=3.64 min; MH$^+$=501

The enantiomers were then separated using a 2×25 cm Chiralpak AD column eluting with 60% ethanol in heptane (0.1% trifluoroacetic acid) with a flow rate of 15 ml/min.

Example 3A (Enantiomer 1) On analytical chiral HPLC (25×0.46 cm Chiralpak AD column, 60% ethanol in heptane with 0.1% trifluoroacetic acid eluting at 1 ml/min) showed a retention time 9.2 min: LCMS: $t_{RET}$=3.71 min; MH$^+$=501

Example 3B (Enantiomer 2) On analytical chiral HPLC (25×0.46 cm Chiralpak AD column, 60% ethanol in heptane with 0.1% trifluoroacetic acid eluting at 1 ml/min) showed a retention time 19.2 min: LCMS: $t_{RET}$=3.71 min; MH$^+$=501

Example 4

2-Chloro-N-ethyl-N-(3,3,3-trifluoro-2-hydroxy-2-{[(1-phenyl-1H-indazol-4-yl)amino]methyl}propyl)benzamide

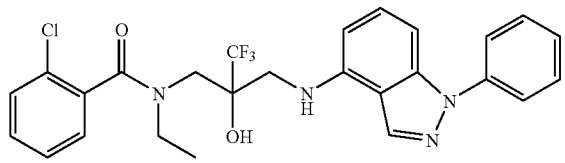

Prepared similarly to Example 1 from 2-chlorobenzoic acid and 3-(ethylamino)-1,1,1-trifluoro-2-{[(1-phenyl-1H-indazol-4-yl)amino]methyl}-2-propanol.

LCMS: $t_{RET}$=3.72 min; MH$^+$=517, 519

Example 5

N-Ethyl-N-[3,3,3-trifluoro-2-({[1-(4-fluorophenyl)-1H-indazol-4-yl]amino}methyl)-2-hydroxypropyl]benzamide

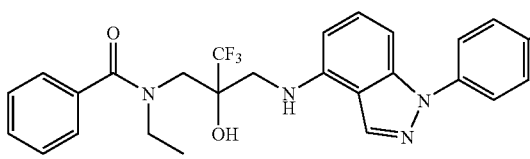

Prepared similarly to Example 1 from benzoic acid and 3-(ethylamino)-1,1,1-trifluoro-2-({[1-(4-fluorophenyl)-1H-indazol-4-yl]amino}methyl)-2-propanol.

LCMS: $t_{RET}$=3.67 min; MH$^+$=501

Example 6

N-Ethyl-2-methyl-N-[3,3,3-trifluoro-2-({[1-(4-fluorophenyl)-1H-indazol-4-yl]amino}methyl)-2-hydroxypropyl]benzamide

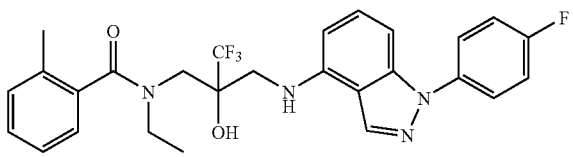

Prepared similarly to Example 1 from 2-methylbenzoic acid and 3-(ethylamino)-1,1,1-trifluoro-2-({[1-(4-fluorophenyl)-1H-indazol-4-yl]amino}methyl)-2-propanol.

LCMS: $t_{RET}$=3.75 min; MH$^+$=515

The enantiomers were then separated using a 2×25 cm Chiralpak AD column eluting with 40% ethanol in heptane with a flow rate of 15 ml/min.

Example 6A (Enantiomer 1) On analytical chiral HPLC (25×0.46 cm Chiralpak AD column, 40% ethanol in heptane eluting at 1 ml/min) showed a retention time 6.9 min:

LCMS: $t_{RET}$=3.82 min; MH$^+$=515

Example 6B (Enantiomer 2) On analytical chiral HPLC (25×0.46 cm Chiralpak AD column, 40% ethanol in heptane eluting at 1 ml/min) showed a retention time 10.8 min:

LCMS: $t_{RET}$=3.82 min; MH$^+$=515

Example 7

N-Ethyl-2-fluoro-N-[3,3,3-trifluoro-2-({[1-(4-fluorophenyl)-1H-indazol-4-yl]amino}methyl)-2-hydroxypropyl]benzamide

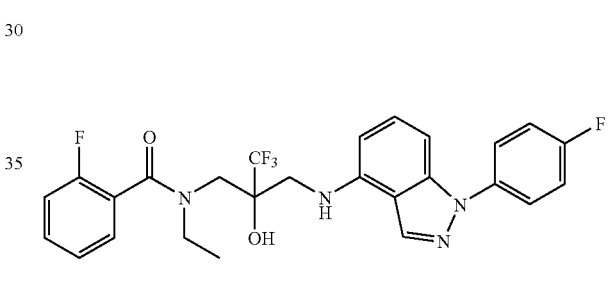

Prepared similarly to Example 1 from 2-fluorobenzoic acid and 3-(ethylamino)-1,1,1-trifluoro-2-({[1-(4-fluorophenyl)-1H-indazol-4-yl]amino}methyl)-2-propanol.

LCMS: $t_{RET}$=3.71 min; MH$^+$=519

The enantiomers were then separated using a 2×25 cm Chiralpak AD column eluting with 50% ethanol in heptane (0.1% trifluoroacetic acid) with a flow rate of 15 ml/min.

Example 7A (Enantiomer 1) On analytical chiral HPLC (25×0.46 cm Chiralpak AD column, 50% ethanol in heptane with 0.1% trifluoroacetic acid eluting at 1 ml/min) showed a retention time 8.96 min: LCMS: $t_{RET}$=3.73 min; MH$^+$=519.

Example 7B (Enantiomer 2) On analytical chiral HPLC (25×0.46 cm Chiralpak AD column, 50% ethanol in heptane with 0.1% trifluoroacetic acid eluting at 1 ml/min) showed a retention time 16.3 min: LCMS: $t_{RET}$=3.73 min; MH$^+$=519.

Example 8

2-Chloro-N-ethyl-N-[3,3,3-trifluoro-2-({[1-(4-fluorophenyl)-1H-indazol-4-yl]amino}methyl)-2-hydroxypropyl]benzamide

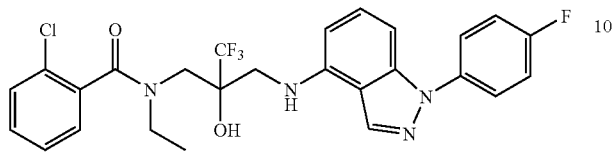

Prepared similarly to Example 1 from 2-chlorobenzoic acid and 3-(ethylamino)-1,1,1-trifluoro-2-({[1-(4-fluorophenyl)-1H-indazol-4-yl]amino}methyl)-2-propanol.

LCMS: $t_{RET}$=3.74 min; MH$^+$=535, 537

Example 9

2-Methyl-N-propyl-N-[3,3,3-trifluoro-2-({[1-(4-fluorophenyl)-1H-indazol-4-yl]amino}methyl)-2-hydroxypropyl]benzamide

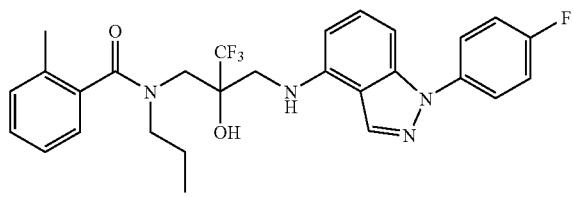

Prepared similarly to Example 1 from 2-methylbenzoic acid and 1,1,1-trifluoro-3-{[1-(4-fluorophenyl)-1H-indazol-4-yl]amino}-2-[(propylamino)methyl]-2-propanol.

LCMS: $t_{RET}$=3.84 min; MH$^+$=529

Example 10

2-Fluoro-N-propyl-N-[3,3,3-trifluoro-2-({[1-(4-fluorophenyl)-1H-indazol-4-yl]amino}methyl)-2-hydroxypropyl]benzamide

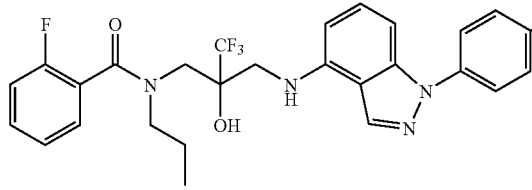

Prepared similarly to Example 1 from 2-fluorobenzoic acid and 1,1,1-trifluoro-3-{[1-(4-fluorophenyl)-1H-indazol-4-yl]amino}-2-[(propylamino)methyl]-2-propanol.

LCMS: $t_{RET}$=3.75 min; MH$^+$=533

Example 11

N-Ethyl-2-methyl-N-(3,3,3-trifluoro-2-hydroxy-2-{[(6-methyl-1-phenyl-1H-indazol-4-yl)amino]methyl}propyl)benzamide

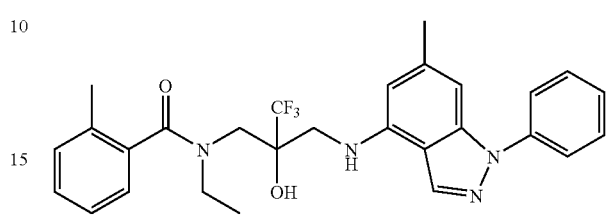

To a solution of 2-methylbenzoic acid (12.7 mg, 0.09 mmol) in N,N-dimethylformamide (100 µl) was added a solution of O-(7-azabenzotriazol-1-yl)-N,N,N',N'-tetramethyluronium hexafluorophosphate (34 mg, 0.09 mmol) in dimethylformamide (150 µl) followed by N,N-diisopropylethylamine (36 µl, 0.21 mmol). The mixture was shaken for 5 minutes and then a solution of 3-(ethylamino)-1,1,1-trifluoro-2-{[(6-methyl-1-phenyl-1H-indazol-4-yl)amino]methyl}-2-propanol (27 mg, 0.07 mmol) in N,N-dimethylformamide (150 µl) was added. The mixture was again shaken for 5 minutes and then left to stand at room temperature for 18 hours. The crude reaction was purified by mass-directed autopreparation (System A) to give the title compound (21.1 mg).

LCMS: $t_{RET}$=3.90 min; MH$^+$=511

Example 12

N-Ethyl-2-fluoro-N-(3,3,3-trifluoro-2-hydroxy-2-{[(6-methyl-1-phenyl-1H-indazol-4-yl)amino]methyl}propyl)benzamide

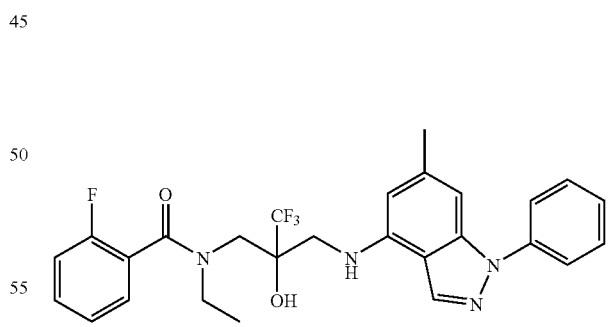

Prepared similarly to Example 11 from 2-fluorobenzoic acid and 3-(ethylamino)-1,1,1-trifluoro-2-{[(6-methyl-1-phenyl-1H-indazol-4-yl-amino]methyl}-2-propanol.

LCMS: $t_{RET}$=3.80 min; MH$^+$=515

Example 13

N-Ethyl-N-(3,3,3-trifluoro-2-hydroxy-2-{[(6-methyl-1-phenyl-1H-indazol-4-yl)amino]methyl}propyl)-3-thiophenecarboxamide

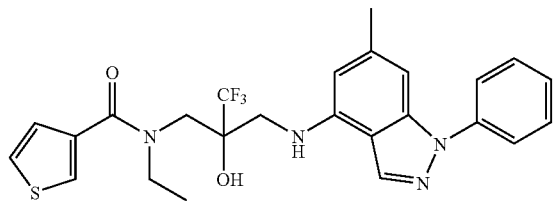

Prepared similarly to Example 11 from 3-thiophenecarboxylic acid and 3-(ethylamino)-1,1,1-trifluoro-2-{[(6-methyl-1-phenyl-1H-indazol-4-yl)amino]methyl}-2-propanol.
LCMS: $t_{RET}$=3.77 min; MH$^+$=503

Example 14

2-Methyl-N-propyl-N-(3,3,3-trifluoro-2-hydroxy-2-{[(6-methyl-1-phenyl-1H-indazol-4-yl)amino]methyl}propyl)benzamide

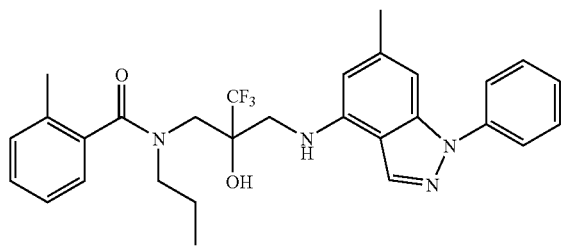

Prepared similarly to Example 11 from 2-methylbenzoic acid and 1,1,1-trifluoro-3-[(6-methyl-1-phenyl-1H-indazol-4-yl)amino]-2-[(propylamino)methyl]-2-propanol.
LCMS: $t_{RET}$=4.00 min; MH$^+$=525

Example 15

2-Fluoro-N-propyl-N-(3,3,3-trifluoro-2-hydroxy-2-{[(6-methyl-1-phenyl-1H-indazol-4-yl)amino]methyl}propyl)benzamide

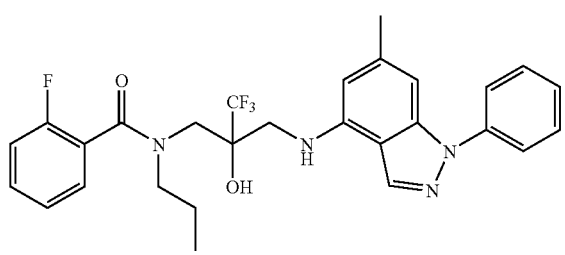

Prepared similarly to Example 11 from 2-fluorobenzoic acid and 1,1,1-trifluoro-3-[(6-methyl-1-phenyl-1H-indazol-4-yl)amino]-2-[(propylamino)methyl]-2-propanol.
LCMS: $t_{RET}$=3.89 min; MH$^+$=529

Example 16

N-Ethyl-N-[3,3,3-trifluoro-2-({[1-(4-fluorophenyl)-6-methyl-1H-indazol-4-yl]amino}methyl)-2-hydroxypropyl]benzamide

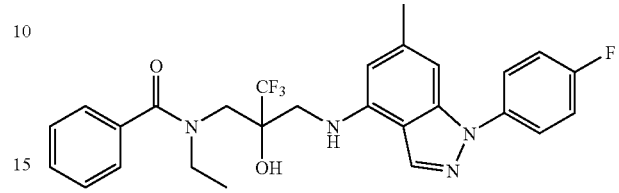

Prepared similarly to Example 1 from benzoic acid and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.84 min; MH$^+$=515

Example 17

N-Ethyl-2-methyl-N-[3,3,3-trifluoro-2-({[1-(4-fluorophenyl)-6-methyl-1H-indazol-4-yl]amino}methyl)-2-hydroxypropyl]benzamide

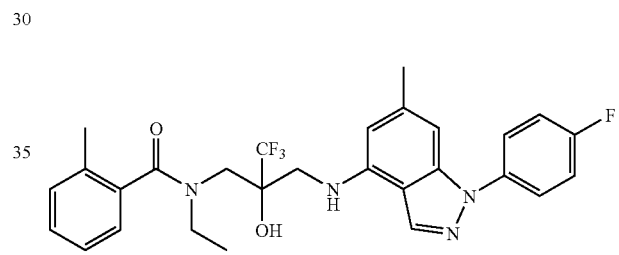

Prepared similarly to Example 1 from 2-methylbenzoic acid and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.92 min; MH$^+$=529

Example 18

N-Ethyl-2-fluoro-N-[3,3,3-trifluoro-2-({[1-(4-fluorophenyl)-6-methyl-1H-indazol-4-yl]amino}methyl)-2-hydroxypropyl]benzamide

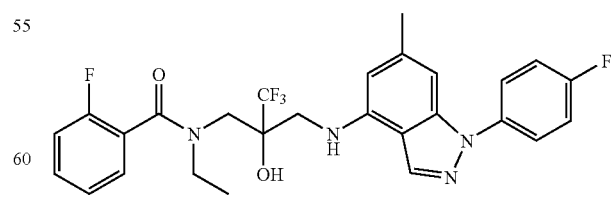

Prepared similarly to Example 1 from 2-fluorobenzoic acid and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.83 min; MH$^+$=533

Example 19

2-Chloro-N-ethyl-N-[3,3,3-trifluoro-2-({[1-(4-fluorophenyl)-6-methyl-1H-indazol-4-yl]amino}methyl)-2-hydroxypropyl]benzamide

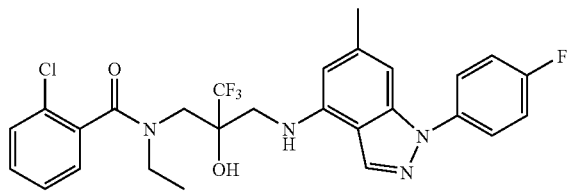

Prepared similarly to Example 1 from 2-chlorobenzoic acid and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.74 min; $MH^+$=549, 551

Example 20

N-Ethyl-N-[3,3,3-trifluoro-2-({[1-(4-fluorophenyl)-6-methyl-1H-indazol-4-yl]amino}methyl)-2-hydroxypropyl]-2-thiophenecarboxamide

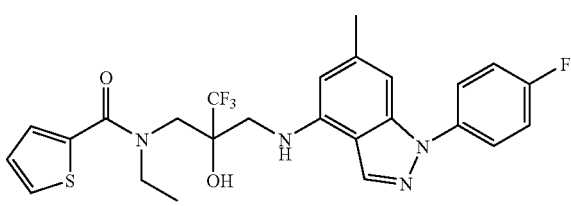

Prepared similarly to Example 1 from 2-thiophenecarboxylic acid and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.85 min; $MH^+$=521

Example 21

N-Ethyl-N-[3,3,3-trifluoro-2-({[1-(4-fluorophenyl)-6-methyl-1H-indazol-4-yl]amino}methyl)-2-hydroxypropyl]-3-thionhenecarboxamide

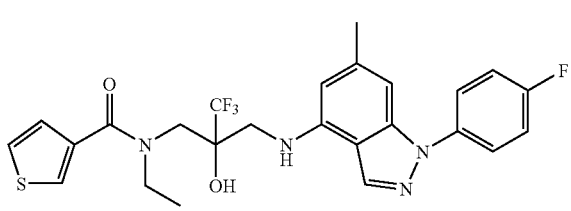

Prepared similarly to Example 1 from 3-thiophenecarboxylic acid and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.79 min; $MH^+$=521

Example 22

N-Propyl-N-[3,3,3-trifluoro-2-({[1-(4-fluorophenyl)-6-methyl-1H-indazol-4-yl]amino}methyl)-2-hydroxypropyl]benzamide

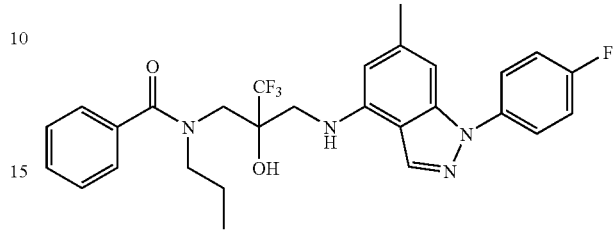

Prepared similarly to Example 1 from benzoic acid and 1,1,1-trifluoro-3-{[1-(4-fluorophenyl)-6-methyl-1H-indazol-4-yl]amino}-2-[(propylamino)methyl]-2-propanol.
LCMS: $t_{RET}$=3.92 min; $MH^+$=529

Example 23

2-Methyl-N-propyl-N-[3,3,3-trifluoro-2-({[1-(4-fluorophenyl)-6-methyl-1H-indazol-4-yl]amino}methyl)-2-hydroxypropyl]benzamide

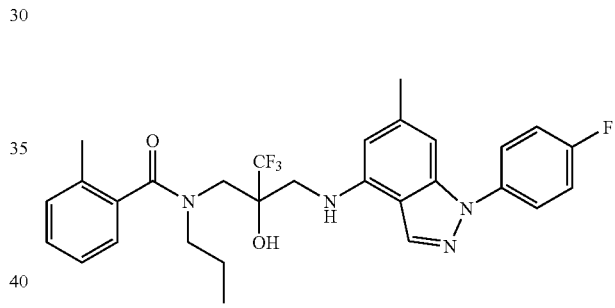

Prepared similarly to Example 1 from 2-methylbenzoic acid and 1,1,1-trifluoro-3-{[1-(4-fluorophenyl)-6-methyl-1H-indazol-4-yl]amino}-2-[(propylamino)methyl]-2-propanol.
LCMS: $t_{RET}$=4.02 min; $MH^+$=543

Example 24

2-Fluoro-N-propyl-N-[3,3,3-trifluoro-2-({[1-(4-fluorophenyl)-6-methyl-1H-indazol-4-yl]amino}methyl)-2-hydroxypropyl]benzamide

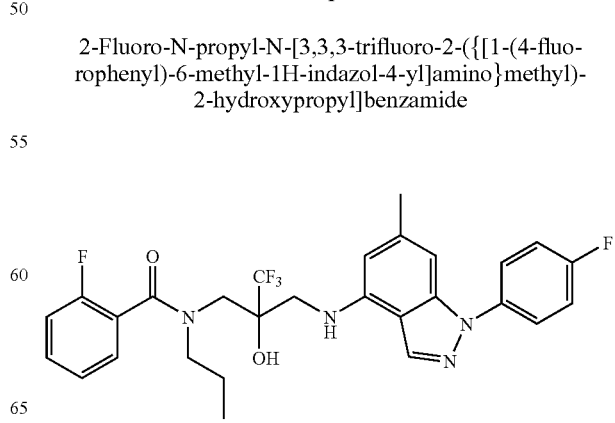

Prepared similarly to Example 1 from 2-fluorobenzoic acid and 1,1,1-trifluoro-3-{[1-(4-fluorophenyl)-6-methyl-1H-indazol-4-yl]amino}-2-[(propylamino)methyl]-2-propanol.
LCMS: $t_{RET}$=3.91 min; MH$^+$=547

Example 25

2-Chloro-N-propyl-N-[3,3,3-trifluoro-2-({[1-(4-fluorophenyl)-6-methyl-1H-indazol-4-yl]amino}methyl)-2-hydroxypropyl]benzamide

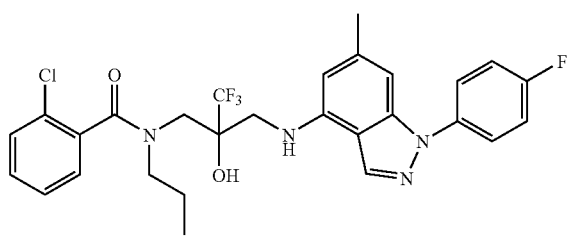

Prepared similarly to Example 1 from 2-chlorobenzoic acid and 1,1,1-trifluoro-3-{[1-(4-fluorophenyl)-6-methyl-1H-indazol-4-yl]amino}-2-[(propylamino)methyl]-2-propanol.
LCMS: $t_{RET}$=3.83 min; MH$^+$=563, 565

Example 26

N-Propyl-N-[3,3,3-trifluoro-2-({[1-(4-fluorophenyl)-6-methyl-1H-indazol-4-yl]amino}methyl)-2-hydroxypropyl]-2-thiophenecarboxamide

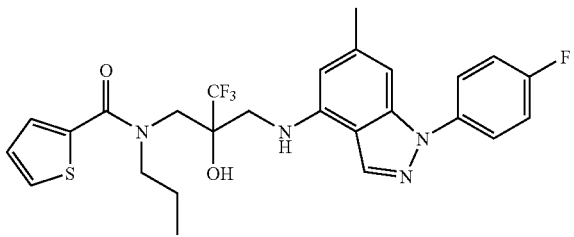

Prepared similarly to Example 1 from 2-thiophenecarboxylic acid and 1,1,1-trifluoro-3-{[1-(4-fluorophenyl)-6-methyl-1H-indazol-4-yl]amino}-2-[(propylamino)methyl]-2-propanol.
LCMS: $t_{RET}$=3.93 min; MH$^+$=535

Example 27

N-Propyl-N-[3,3,3-trifluoro-2-({[1-(4-fluorophenyl)-6-methyl-1H-indazol-4-yl]amino}methyl)-2-hydroxypropyl]-3-thiophenecarboxamide

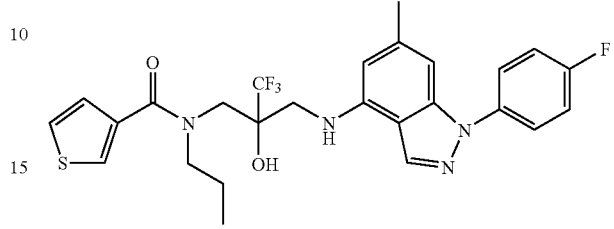

Prepared similarly to Example 1 from 3-thiophenecarboxylic acid and 1,1,1-trifluoro-3-{[1-(4-fluorophenyl)-6-methyl-1H-indazol-4-yl]amino}-2-[(propylamino)methyl]-2-propanol.
LCMS: $t_{RET}$=3.88 min; MH$^+$=535

Example 28

N-Ethyl-N-(3,3,3-trifluoro-2-hydroxy-2-{[(6-methyl-1-phenyl-1H-indazol-4-yl)amino]methyl}propyl)benzamide

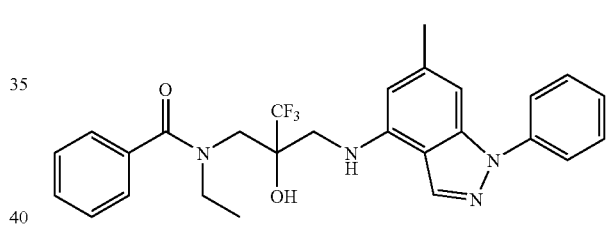

Prepared similarly to Example 11 from benzoic acid and 3-(ethylamino)-1,1,1-trifluoro-2-{[(6-methyl-1-phenyl-1H-indazol-4-yl)amino]methyl}-2-propanol.
LCMS: $t_{RET}$=3.76 min; MH$^+$=497

Example 29

2-Chloro-N-ethyl-N-(3,3,3-trifluoro-2-hydroxy-2-{[(6-methyl-1-phenyl-1H-indazol-4-yl)amino]methyl}propyl)benzamide

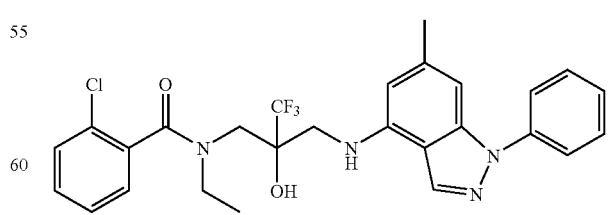

Prepared similarly to Example 11 from 2-chlorobenzoic acid and 3-(ethylamino)-1,1,1-trifluoro-2-{[(6-methyl-1-phenyl-1H-indazol-4-yl)amino]methyl}-2-propanol.
LCMS: $t_{RET}$=3.83 min; MH$^+$=531, 533

Example 30

N-Ethyl-N-(3,3,3-trifluoro-2-hydroxy-2-{[(1-phenyl-1H-indazol-4-yl)amino]methyl}propyl)-2-thiophenecarboxamide

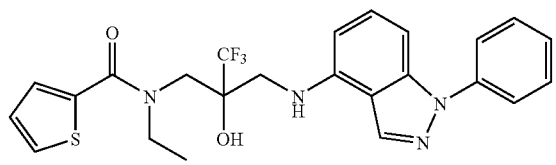

Prepared similarly to Example 1 from 2-thiophenecarboxylic acid and 3-(Ethylamino)-1,1,1-trifluoro-2-{[(1-phenyl-1H-indazol-4-yl)amino]methyl}-2-propanol.

LCMS: $t_{RET}$=3.70 min; MH$^+$=489

Example 31

N-Ethyl-N-(3,3,3-trifluoro-2-hydroxy-2-{[1(1-phenyl-1H-indazol-4-yl)amino]methyl}propyl)-3-thiophenecarboxamide

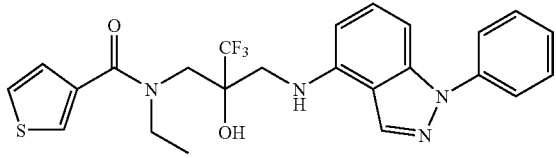

Prepared similarly to Example 1 from 3-thiophenecarboxylic acid and 3-(ethylamino)-1,1,1-trifluoro-2-{[(1-phenyl-1H-indazol-4-yl)amino]methyl}-2-propanol.

LCMS: $t_{RET}$=3.60 min; MH$^+$=489

Example 32

N-Propyl-N-(3,3,3-trifluoro-2-hydroxy-2-{[(1-phenyl-1H-indazol-4-yl)amino]methyl}propyl)benzamide

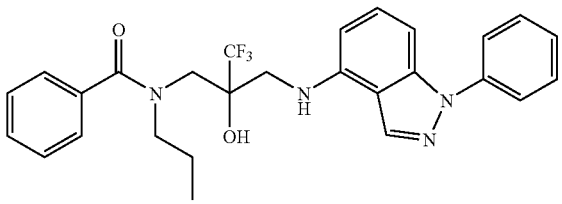

Prepared similarly to Example 1 from benzoic acid and 1,1,1-trifluoro-3-[(1-phenyl-1H-indazol-4-yl)amino]-2-[(propylamino)methyl]-2-propanol.

LCMS: $t_{RET}$=3.74 min; MH$^+$=497

Example 33

2-Methyl-N-propyl-N-(3,3,3-trifluoro-2-hydroxy-2-{[(1-phenyl-1H-indazol-4-yl)amino]methy}propyl)benzamide

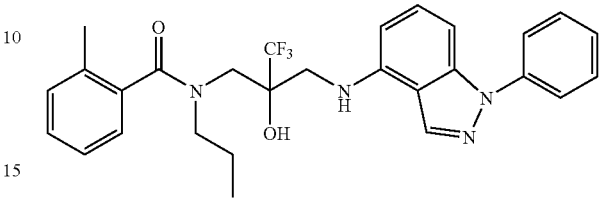

Prepared similarly to Example 1 from 2-methylbenzoic acid and 1,1,1-trifluoro-3-[(1-phenyl-1H-indazol-4-yl)amino]-2-[(propylamino)methyl]-2-propanol.

LCMS: $t_{RET}$=3.83 min; MH$^+$=511

Example 34

2-Fluoro-N-propyl-N-(3,3,3-trifluoro-2-hydroxy-2-{[(1-phenyl-1H-indazol-4-yl)amino]methyl}propyl)benzamide

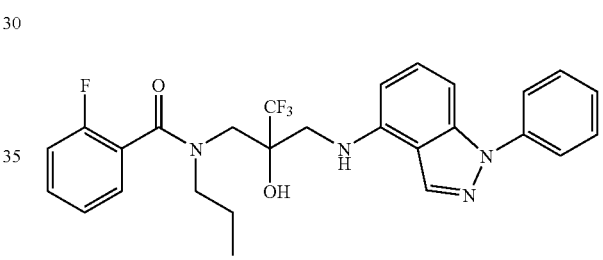

Prepared similarly to Example 1 from 2-fluorobenzoic acid and 1,1,1-trifluoro-3-[(1-phenyl-1H-indazol-4-yl)amino]-2-[(propylamino)methyl]-2-propanol.

LCMS: $t_{RET}$=3.73 min; MH$^+$=515

Example 35

2-Chloro-N-propyl-N-(3,3,3-trifluoro-2-hydroxy-2-{[(1-phenyl-1H-indazol-4-yl)amino]methyl}propyl)benzamide

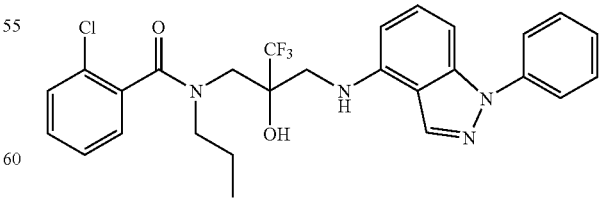

Prepared similarly to Example 1 from 2-chlorobenzoic acid and 1,1,1-trifluoro-3-[(1-phenyl-1H-indazol-4-yl)amino]-2-[(propylamino)methyl]-2-propanol.

LCMS: $t_{RET}$=3.82 min; MH$^+$=531, 533

Example 36

N-Propyl-N-(3,3,3-trifluoro-2-hydroxy-2-{[(1-phenyl-1H-indazol-4-yl)amino]methyl}propyl)-2-thiophenecarboxamide

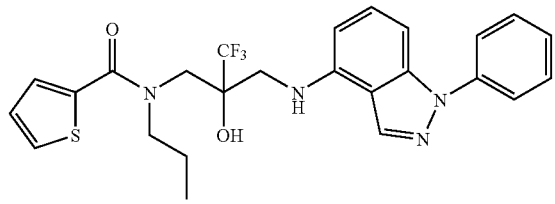

Prepared similarly to Example 1 from 2-thiophenecarboxylic acid and 1,1,1-trifluoro-3-[(1-phenyl-1H-indazol-4-yl)amino]-2-[(propylamino)methyl]-2-propanol.

LCMS: $t_{RET}$=3.83 min; MH$^+$=503

Example 37

N-Propyl-N-(3,3,3-trifluoro-2-hydroxy-2-{[(1-phenyl-1H-indazol-4-yl)amino]methyl}propyl)-3-thiophenecarboxamide

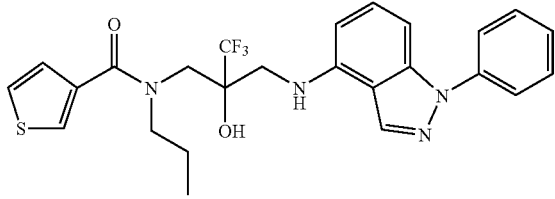

Prepared similarly to Example 1 from 3-thiophenecarboxylic acid and 1,1,1-trifluoro-3-[(1-phenyl-1H-indazol-4-yl)amino]-2-[(propylamino)methyl]-2-propanol.

LCMS: $t_{RET}$=3.71 min; MH$^+$=503

Example 38

N-Ethyl-N-[3,3,3-trifluoro-2-({[1-(4-fluorophenyl)-1H-indazol-4-yl]amino}methyl)-2-hydroxypropyl]-2-thiophenecarboxamide

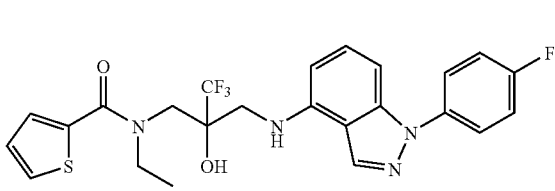

Prepared similarly to Example 1 from 2-thiophenecarboxylic acid and 3-(ethylamino)-1,1,1-trifluoro-2-({[1-(4-fluorophenyl)-1H-indazol-4-yl]amino}methyl)-2-propanol.

LCMS: $t_{RET}$=3.67 min; MH$^+$=507

Example 39

N-Ethyl-N-[3,3,3-trifluoro-2-({[1-(4-fluorophenyl)-1H-indazol-4-yl]amino}methyl)-2-hydroxypropyl]-3-thiophenecarboxamide

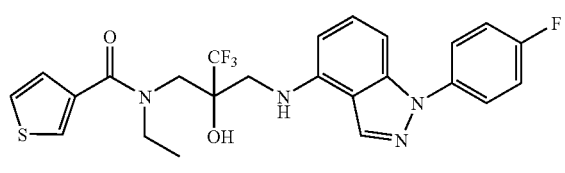

Prepared similarly to Example 1 from 3-thiophenecarboxylic acid and 3-(ethylamino)-1,1,1-trifluoro-2-({[1-(4-fluorophenyl)-1H-indazol-4-yl]amino}methyl)-2-propanol.

LCMS: $t_{RET}$=3.62 min; MH$^+$=507

Example 40

N-Propyl-N-[3,3,3-trifluoro-2-({[1-(4-fluorophenyl)-1H-indazol-4-yl]amino}methyl)-2-hydroxypropyl]benzamide

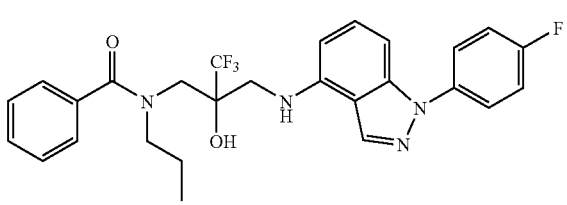

Prepared similarly to Example 1 from benzoic acid and 1,1,1-trifluoro-3-{[1-(4-fluorophenyl)-1H-indazol-4-yl]amino}-2-[(propylamino)methyl]-2-propanol.

LCMS: $t_{RET}$=3.76 min; MH$^+$=515

Example 41

2-Chloro-N-propyl-N-[3,3,3-trifluoro-2-({[1-(4-fluorophenyl)-1H-indazol-4-yl]amino}methyl)-2-hydroxypropyl]benzamide

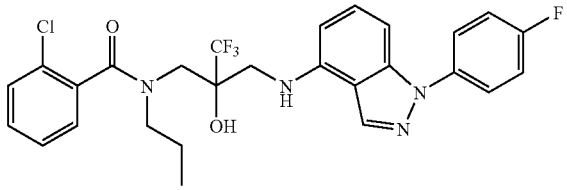

Prepared similarly to Example 1 from 2-chlorobenzoic acid and 1,1,1-trifluoro-3-{[1-(4-fluorophenyl)-1H-indazol-4-yl]amino}-2-[(propylamino)methyl]-2-propanol LCMS: $t_{RET}$=3.83 min; MH$^+$=549, 551.

Example 42

N-Propyl-N-[3,3,3-trifluoro-2-({[1-(4-fluorophenyl)-1H-indazol-4-yl]amino}methyl)-2-hydroxypropyl]-2-thiophenecarboxamide

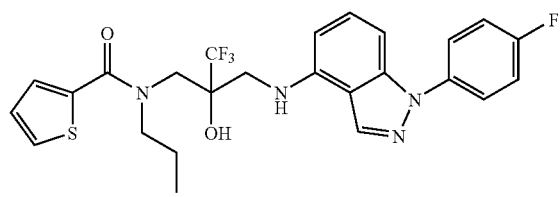

Prepared similarly to Example 1 from 2-thiophenecarboxylic acid and 1,1,1-trifluoro-3-{[1-(4-fluorophenyl)-1H-indazol-4-yl]amino}-2-[(propylamino)methyl]-2-propanol.
LCMS: $t_{RET}$=3.76 min; MH$^+$=521

Example 43

N-Propyl-N-[3,3,3-trifluoro-2-({[1-(4-fluorophenyl)-1H-indazol-4-yl]amino}methyl)-2-hydroxypropyl]-3-thiophenecarboxamide

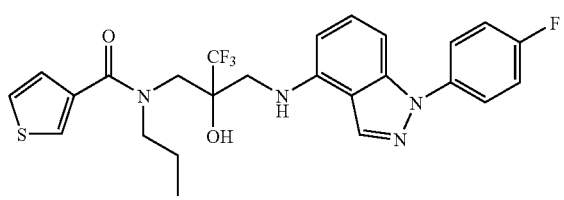

Prepared similarly to Example 1 from 3-thiophenecarboxylic acid and 1,1,1-trifluoro-3-{[1-(4-fluorophenyl)-1H-indazol-4-yl]amino}-2-[(propylamino)methyl]-2-propanol.
LCMS: $t_{RET}$=3.71 min; MH$^+$=521

Example 44

N-Ethyl-N-(3,3,3-trifluoro-2-hydroxy-2-{[(6-methyl-1-phenyl-1H-indazol-4-yl)amino]methyl}propyl)-2-thiophenecarboxamide

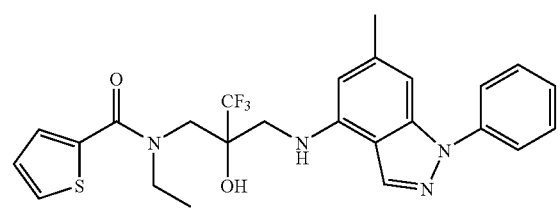

Prepared similarly to Example 11 from 2-thiophenecarboxylic acid and 3-(ethylamino)-1,1,1-trifluoro-2-{[(6-methyl-1-phenyl-1H-indazol-4-yl)amino]methyl}-2-propanol.
LCMS: $t_{RET}$=3.82 min; MH$^+$=503

Example 45

N-Propyl-N-(3,3,3-trifluoro-2-hydroxy-2-{[(6-methyl-1-phenyl-1H-indazol-4-yl)amino]methyl}propyl)benzamide

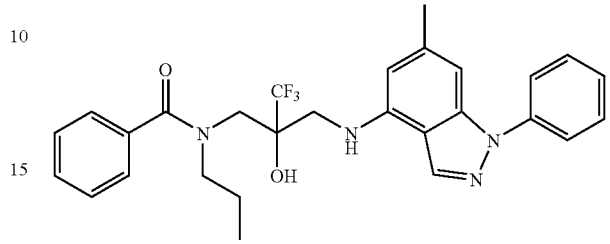

Prepared similarly to Example 11 from benzoic acid and 1,1,1-trifluoro-3-[(6-methyl-1-phenyl-1H-indazol-4-yl)amino]-2-[(propylamino)methyl]-2-propanol.
LCMS: $t_{RET}$=3.90 min; MH$^+$=511

Example 46

N-Propyl-N-(3,3,3-trifluoro-2-hydroxy-2-{[(6-methyl-1-phenyl-1H-indazol-4-yl)amino]methyl}propyl)-2-thiophenecarboxamide

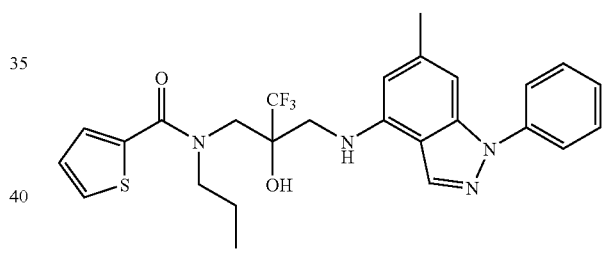

Prepared similarly to Example 11 from 2-thiophenecarboxylic acid and 1,1,1-trifluoro-3-[(6-methyl-1-phenyl-1H-indazol-4-yl)amino]-2-[(propylamino)methyl]-2-propanol.
LCMS: $t_{RET}$=3.92 min; MH$^+$=517

Example 47

N-Propyl-N-(3,3,3-trifluoro-2-hydroxy-2-{[(6-methyl-1-phenyl-1H-indazol-4-yl)amino]methyl}propyl)-3-thiophenecarboxamide

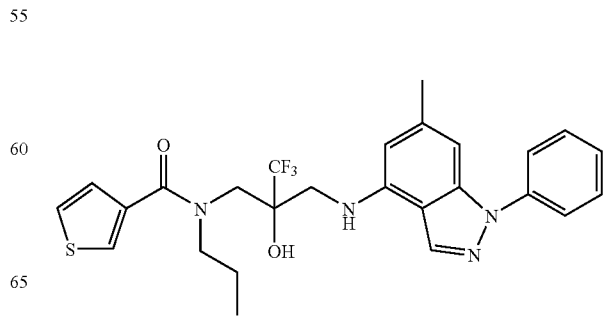

Prepared similarly to Example 11 from 3-thiophenecarboxylic acid and 1,1,1-trifluoro-3-[(6-methyl-1-phenyl-1H-indazol-4-yl)amino]-2-[(propylamino)methyl]-2-propanol.

LCMS: $t_{RET}$=3.86 min; MH$^+$=517

Example 48

N-Ethyl-2,6-dimethyl-N-[3,3,3-trifluoro-2-({[1-(4-fluorophenyl)-1H-indazol-4-yl]amino}methyl)-2-hydroxypropyl]benzamide

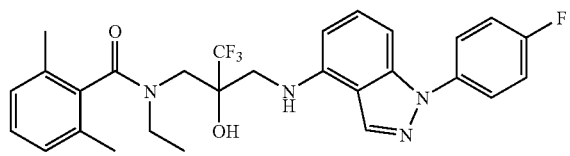

3-(Ethylamino)-1,1,1-trifluoro-2-({[1-(4-fluorophenyl)-1H-indazol-4-yl]amino}methyl)-2-propanol (25 mg, 0.063 mmol) was dissolved in anhydrous dichloromethane (0.15 ml). N,N-diisopropylethylamine (0.011 ml, 0.13 mmol) was then added followed by 2,6-dimethylbenzoyl chloride in DCM (10.6 mg, 0.065 mmol as a 100 µl aliquot of 80.8 mg in 0.76 ml DCM) and the mixture stirred at room temperature overnight. The mixture was diluted with dichloromethane, washed successively with aqueous sodium bicarbonate and water and then dried through a hydrophobic frit and evaporated and the crude product purified by mass directed autopreparation (System B). Product containing fractions were partitioned between dichloromethane and aqueous sodium bicarbonate. The aqueous layer was re-extracted with dichloromethane and the combined organic extracts were washed successively water and brine, dried through a hydrophobic frit and evaporated in vacuo to give the title compound (13.1 mg).

LCMS: $t_{RET}$=3.99 min; MH$^+$=529

Example 49

N-Ethyl-2,6-dimethyl-N-[3,3,3-trifluoro-2-({[1-(4-fluorophenyl)-6-methyl-1H-indazol-4-yl]amino}methyl)-2-hydroxypropyl]benzamide

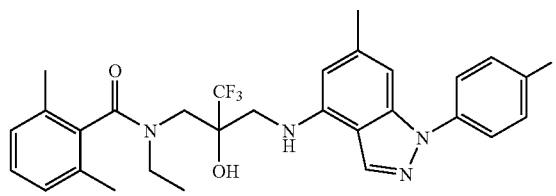

Prepared similarly to Example 48 from 2,6-dimethylbenzoyl chloride and 3-(ethylamino)-1,1,1-trifluoro-2-({[1-(4-fluorophenyl)-6-methyl-1H-indazol-4-yl]amino}methyl)-2-propanol.

LCMS: $t_{RET}$=4.06 min; MH$^+$=543

Example 50

N-Ethyl-2,6-difluoro-N-[3,3,3-trifluoro-2-({[1-(4-fluorophenyl)-1H-indazol-4-yl]amino}methyl)-2-hydroxypropyl]benzamide

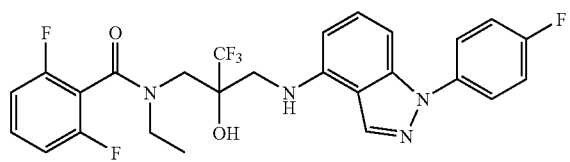

Prepared similarly to Example 48 from 2,6-difluorobenzoyl chloride and 3-(ethylamino)-1,1,1-trifluoro-2-({[1-(4-fluorophenyl)-1H-indazol-4-yl]amino}methyl)-2-propanol.

LCMS: $t_{RET}$=3.84 min; MH$^+$=537

Example 51

N-ethyl-2,6-difluoro-N-[3,3,3-trifluoro-2-({[1-(4-fluorophenyl)-6-methyl-1H-indazol-4-yl]amino}methyl)-2-hydroxypropyl]benzamide

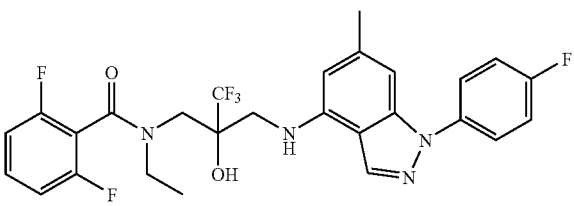

Prepared similarly to Example 48 from 2,6-difluorobenzoyl chloride and 3-(ethylamino)-1,1,1-trifluoro-2-({[1-(4-fluorophenyl)-6-methyl-1H-indazol-4-yl]amino}methyl)-2-propanol.

LCMS: $t_{RET}$=3.91 min; MH$^+$=551

Example 52

2,6-Dichloro-N-ethyl-N-[3,3,3-trifluoro-2-({[1-(4-fluorophenyl)-1H-indazol-4-yl]amino}methyl)-2-hydroxypropyl]benzamide

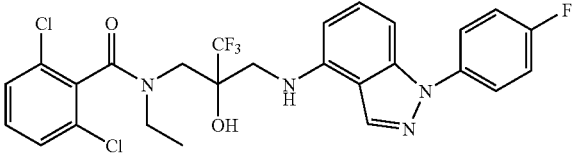

3-(Ethylamino)-1,1,1-trifluoro-2-({[1-(4-fluorophenyl)-1H-indazol-4-yl]amino}methyl)-2-propanol (30 mg, 0.76 mmol) was dissolved in dry DCM (4 ml). N,N-diisopropylethylamine (294 µl, 1.51 mmol) was then added followed by 2,6-dimethylbenzoyl chloride (118 µl, 0.76 mmol). The reaction was stirred under nitrogen at ambient temperature overnight. The mixture was washed successively with aqueous sodium bicarbonate and water and then dried through a hydrophobic frit and evaporated and the crude product (yellow foam) purified by mass directed autopreparation (System B). Product containing fractions were partitioned between dichloromethane and aqueous sodium bicarbonate. The aqueous layer was re-extracted with dichloromethane and the combined organic extracts were washed successively water and brine, dried through a hydrophobic frit and evaporated in vacuo to give the title compound as a yellow oil (0.39 g, 90%).

LCMS: $t_{RET}$=4.0 min; MH$^+$=569, 571, 573

This mixture of enantiomers (30 mg) was then separated using a 2×25 cm Chiralpak AD column eluting with 40% ethanol in heptane with a flow rate of 15 ml/min.

Example 52A (Enantiomer 1) On analytical chiral HPLC (25×0.46 cm Chiralpak AD column, 40% ethanol in heptane eluting at 1 ml/min) showed a retention time 5.4 min:

LCMS: $t_{RET}$=4.05 min; MH$^+$=569, 571, 573

Example 52B (Enantiomer 2) On analytical chiral HPLC (25×0.46 cm Chiralpak AD column, 40% ethanol in heptane eluting at 1 ml/min) showed a retention time 9.1 min:

LCMS: $t_{RET}$=4.05 min; MH$^+$=569, 571, 573

Example 53

2,6-Dichloro-N-ethyl-N-[3,3,3-trifluoro-2-({[1-(4-fluorophenyl)-6-methyl-1H-indazol-4-yl]amino}methyl)-2-hydroxypropyl]benzamide

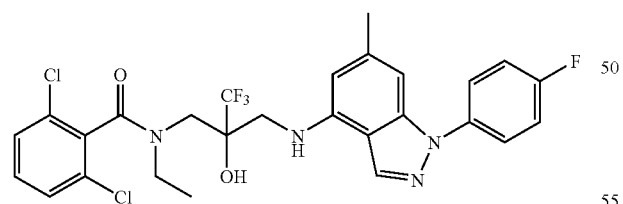

Prepared similarly to Example 48 from 2,6-dichlororobenzoyl chloride and 3-(ethylamino)-1,1,1-trifluoro-2-({[1-(4-fluorophenyl)-6-methyl-1H-indazol-4-yl]amino}methyl)-2-propanol.

LCMS: $t_{RET}$=3.97 min; MH$^+$=583, 585, 587

Example 54

2-Chloro-N-ethyl-6-fluoro-N-[3,3,3-trifluoro-2-({[1-(4-fluorophenyl)-1H-indazol-4-yl]amino}methyl)-2-hydroxypropyl]benzamide

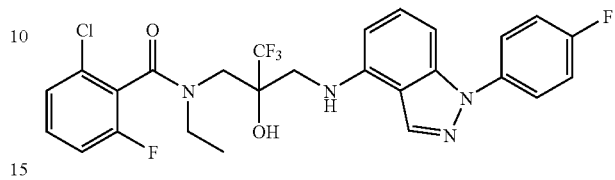

Prepared similarly to Example 48 from 2-chloro-6-fluorobenzoylchloride and 1,1,1-trifluoro-3-{[1-(4-fluorophenyl)-1H-indazol-4-yl]amino}-2-[(propylamino)methyl]-2-propanol.

LCMS: $t_{RET}$=3.85 min; MH$^+$=553, 555

Example 55

2-Chloro-N-ethyl-6-fluoro-N-[3,3,3-trifluoro-2-({[1-(4-fluorophenyl)-6-methyl-1H-indazol-4-yl]amino}methyl)-2-hydroxypropyl]benzamide

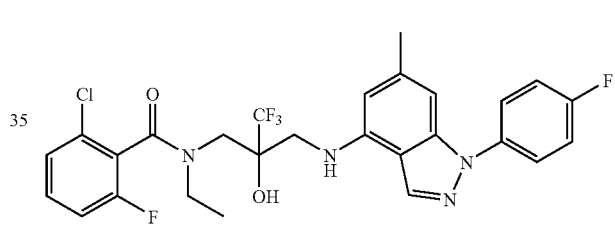

Prepared similarly to Example 48 from 2-chloro-6-fluorobenzoylchloride and 3-(ethylamino)-1,1,1-trifluoro-2-({[1-(4-fluorophenyl)-6-methyl-1H-indazol-4-yl]amino}methyl)-2-propanol.

LCMS: $t_{RET}$=3.91 min; MH$^+$=567, 569

Example 56

2-Chloro-N-ethyl-6-methyl-N-[3,3,3-trifluoro-2-({[1-(4-fluorophenyl)-1H-indazol-4-yl]amino}methyl)-2-hydroxypropyl]benzamide

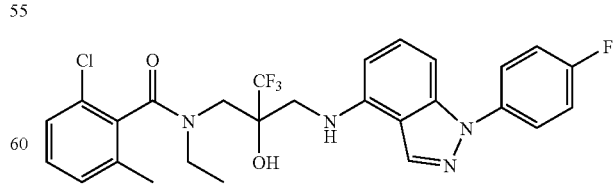

Prepared similarly to Example 48 by reaction of 2-chloro-6-methylbenzoylchloride and 1,1,1-trifluoro-3-{[1-(4-fluorophenyl)-1H-indazol-4-yl]amino}-2-[(propylamino)methyl]-2-propanol in chloroform over 42 hours. Purification by mass directed autopreparation (System B) resulted in separation of atropisomers of the title compound:

Example 56A (Racemic atropisomer 1) LCMS: $t_{RET}$=3.95 min; MH$^+$=549, 551

Example 56B (Racemic atropisomer 2) LCMS: $t_{RET}$=4.00 min; MH$^+$=549, 551

Example 57

2-Chloro-N-ethyl-6-methyl-N-[3,3,3-trifluoro-2-({[1-(4-fluorophenyl)-6-methyl-1H-indazol-4-yl]amino}methyl)-2-hydroxypropyl]benzamide

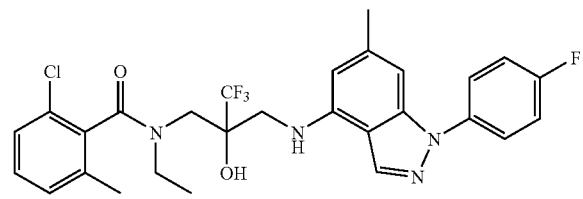

Prepared similarly to Example 56 from 2-chloro-6-methylbenzoylchloride and 3-(ethylamino)-1,1,1-trifluoro-2-({[1-(4-fluorophenyl)-6-methyl-1H-indazol-4-yl]amino}methyl)-2-propanol. Purification by mass directed autopreparation (System B) resulted in separation of atropisomers of the title compound:

Example 57A (Racemic atropisomer 1) LCMS: $t_{RET}$=4.01 min; MH$^+$=563, 565

Example 57B (Racemic atropisomer 2) LCMS: $t_{RET}$=4.06 min; MH$^+$=563, 565

Example 58

N-Ethyl-2-fluoro-N-[3,3,3-trifluoro-2-({[1-(4-fluorophenyl)-1H-indazol-4-yl]amino}methyl)-2-hydroxypropyl]-6-(trifluoromethyl)benzamide

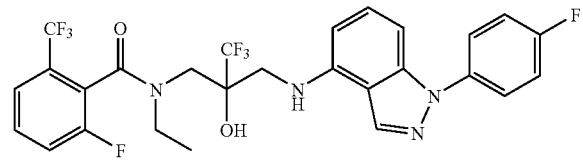

Prepared similarly to Example 48 from 2-fluoro-6-(trifluoromethyl)benzoyl chloride and 1,1,1-trifluoro-3-{[1-(4-fluorophenyl)-1H-indazol-4-yl]amino}-2-[(propylamino)methyl]-2-propanol.
LCMS: $t_{RET}$=3.86 min; MH$^+$=587

Example 59

N-Ethyl-2-fluoro-N-[3,3,3-trifluoro-2-({[1-(4-fluorophenyl)-6-methyl-1H-indazol-4-yl]amino}methyl)-2-hydroxypropyl]-6-(trifluoromethyl)benzamide

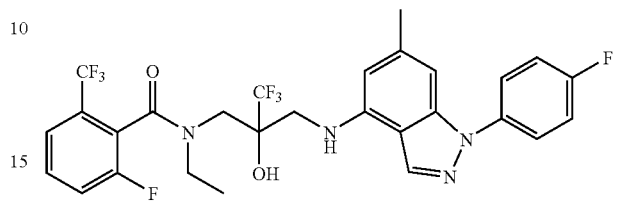

Prepared similarly to Example 48 from 2-fluoro-6-(trifluoromethyl)benzoyl chloride and 3-(ethylamino)-1,1,1-trifluoro-2-({[1-(4-fluorophenyl)-6-methyl-1H-indazol-4-yl]amino}methyl)-2-propanol.
LCMS: $t_{RET}$=3.93 min; MH$^+$=601

Biological Experimental

Glucocorticoid Receptor Binding Assay

The ability of compounds to bind to the glucocorticoid receptor was determined by assessing their ability to compete with an Alexa 555 fluorescently-labelled dexamethasone derivative. Compounds were solvated and diluted in DMSO, and transferred directly into assay plates. Fluorescent dexamethasone and a partially purified full length glucocorticoid receptor were added to the plates, together with buffer components to stabilise the GR protein (including stabilisation peptide (Panvera catalogue number P2815)) and incubated at room temperature for 2 hours in the dark. Binding of each compound was assessed by analysing the displacement of fluorescent ligand by measuring the decrease in fluorescence polarisation signal from the mixture.

Examples 1 to 59 show glucocorticoid binding with a $pIC_{50} \geq 7$ in this assay.

Glucocorticoid Mediated Transrepression of NFκB Activity

Human A549 lung epithelial cells were engineered to contain a secreted placental alkaline phosphatase gene under the control of the distal region of the NFκB dependent ELAM promoter as previously described in Ray, K. P., Farrow, S., Daly, M., Talabot, F. and Searle, N. "Induction of the E-selectin promoter by interleukin 1 and tumour necrosis factor alpha, and inhibition by glucocorticoids" *Biochemical Journal* (1997) 328: 707-15.

Compounds were solvated and diluted in DMSO, and transferred directly into assay plates such that the final concentration of DMSO was 0.7%. Following the addition of cells (40K per well), plates were incubated for 1 hour prior to the addition of 3 ng/ml human recombinant TNFα. Following continued incubation for 16 hours, alkaline phosphatase activity was determined by measuring the change in optical density at 405 nM with time following the addition of 0.7 volumes of assay buffer (1 mg/ml p-nitrophenylphosphate dissolved in 1M diethanolamine, 0.28M NaCl, 0.5 mM $MgCl_2$). Dose response curves were constructed from which $EC_{50}$ values were estimated.

Examples 1 to 3, 3A, 4 to 6, 6A, 7, 7A, 8 to 59 show $pEC_{50} \geq 8.0$ in this assay.

Assay for Progesterone Receptor Activity

A T225 flask of CV-1 cells at a density of 80% confluency was washed with PBS, detached from the flask using 0.25% trypsin and counted using a Sysmex KX-21N. Cells were diluted in DMEM containing 10% Hyclone, 2 mM L-Glutamate and 1% Pen/Strep at 140 cells/µl and transduced with 10% PRb-BacMam and 10% MMTV-BacMam. 70 ml of suspension cells were dispensed to each well of white Nunc 384-well plates, containing compounds at the required concentration. After 24 h 10 µl of Steadylite were added to each well of the plates. Plates were incubated in the dark for 10 min before reading them on a Viewlux reader. Dose response curves were constructed from which $pEC_{50}$ values were estimated.

Examples 1 to 17, 20 to 50, 52 to 54 and 56A to 58, show $pEC_{50} < 6$ in this assay.

In describing examples according to their activity in the assays above, it will be appreciated that at least one isomer, for example, an enantiomer in a mixture of isomers (such as a racemate) has the described activity. The other enantiomer may have similar activity, less activity, no activity or may have some antagonist activity in the case of a functional assay.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

What is claimed is:

1. A compound of formula (I):

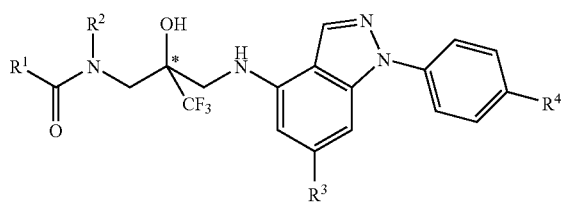

* = chiral centre wherein
$R^1$ is thienyl or

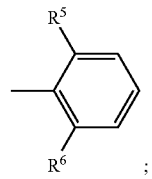

$R^2$ is ethyl or n-propyl;
$R^3$ is hydrogen or methyl;
$R^4$ is hydrogen or fluorine;
$R^5$ and $R^6$ are each independently hydrogen, methyl, fluorine, chlorine or trifluoromethyl; or a salt thereof.

2. A compound according to claim 1 wherein $R^1$ is

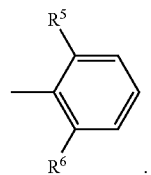

3. A compound according to claim 1 wherein $R^2$ is ethyl.
4. A compound according to claim 1 wherein $R^3$ is hydrogen.
5. A compound according to claim 1 wherein $R^4$ is fluorine.
6. A compound according to claim 1 wherein $R^5$ is hydrogen and $R^6$ is methyl, fluorine or chlorine.
7. A compound according to claim 1 wherein $R^5$ and $R^6$ are both fluorine or both chlorine.
8. A compound which is selected from the group consisting of:
   N-ethyl-2-methyl-N-[3,3,3-trifluoro-2-({[1-(4-fluorophenyl)-1H-indazol-4-yl]amino}methyl)-2-hydroxypropyl]benzamide;
   N-ethyl-2-fluoro-N-[3,3,3-trifluoro-2-({[1-(4-fluorophenyl)-1H-indazol-4-yl]amino}methyl)-2-hydroxypropyl]benzamide;
   2,6-dichloro-N-ethyl-N-[3,3,3-trifluoro-2-({[1-(4-fluorophenyl)-1H-indazol-4-yl]amino}methyl)-2-hydroxypropyl]benzamide; and a salt thereof.
9. A method of treating an inflammatory and/or allergic condition in a human or animal subject in need thereof, which method comprises administering to said human or animal subject an effective amount of a compound as claimed in claim 1, or a pharmaceutically acceptable salt thereof.
10. A method of treating rheumatoid arthritis, asthma, COPD, allergy and/or rhinitis in a human or animal subject in need thereof, which method comprises administering to said human or animal subject an effective amount of a compound as claimed in claim 1, or a pharmaceutically acceptable salt thereof.

* * * * *